United States Patent
Sessler et al.

(10) Patent No.: US 12,077,520 B2
(45) Date of Patent: Sep. 3, 2024

(54) COMPOUNDS FOR THE SELECTIVE SOLID-LIQUID EXTRACTION AND LIQUID-LIQUID EXTRACTION OF LITHIUM CHLORIDE

(71) Applicants: BOARD OF REGENTS, THE UNIVERSITY OF THE TEXAS SYSTEM, Austin, TX (US); GYEONGSANG NATIONAL UNIVERSITY, Jinju-si (KR)

(72) Inventors: Jonathan L. Sessler, Austin, TX (US); Qing He, Austin, TX (US); Sung Kuk Kim, Jinju-si (KR)

(73) Assignees: Board of Regents, The University of Texas System, Austin, TX (US); GYEONGSANG NATIONAL UNIVERSITY, Jinju-si (KR)

( * ) Notice: Subject to any disclaimer, the term of this patent is extended or adjusted under 35 U.S.C. 154(b) by 834 days.

(21) Appl. No.: 17/057,713

(22) PCT Filed: May 23, 2019

(86) PCT No.: PCT/US2019/033690
§ 371 (c)(1),
(2) Date: Nov. 23, 2020

(87) PCT Pub. No.: WO2019/226863
PCT Pub. Date: Nov. 28, 2019

(65) Prior Publication Data
US 2022/0274956 A1  Sep. 1, 2022

Related U.S. Application Data

(60) Provisional application No. 62/675,558, filed on May 23, 2018.

(51) Int. Cl.
| | | |
|---|---|---|
| *C07D 401/14* | (2006.01) | |
| *B01D 11/04* | (2006.01) | |
| *C01D 15/04* | (2006.01) | |
| *C07D 471/04* | (2006.01) | |
| *C22B 3/16* | (2006.01) | |
| *C22B 3/36* | (2006.01) | |
| *C22B 26/12* | (2006.01) | |

(52) U.S. Cl.
CPC ........ *C07D 401/14* (2013.01); *B01D 11/0492* (2013.01); *C01D 15/04* (2013.01); *C07D 471/04* (2013.01); *C22B 3/1666* (2013.01); *C22B 3/36* (2021.05); *C22B 26/12* (2013.01)

(58) Field of Classification Search
CPC .................................................. C07D 401/14
USPC ....................................................... 546/88
See application file for complete search history.

(56) References Cited

U.S. PATENT DOCUMENTS

| | | |
|---|---|---|
| 6,262,257 B1 | 7/2001 | Gale et al. |
| 6,984,734 B2 | 1/2006 | Sessler et al. |
| 7,041,819 B2 | 5/2006 | Sessler et al. |
| 7,122,572 B2 | 10/2006 | Gale et al. |
| 8,802,074 B2 | 8/2014 | Sessler et al. |
| 2010/0120958 A1 | 5/2010 | Qin et al. |
| 2010/0129308 A1 | 5/2010 | Sessler et al. |
| 2014/0239221 A1 | 8/2014 | Harrison et al. |

OTHER PUBLICATIONS

Chandler et al., "Synthesis of some 2,9-disubstituted-1,10-phenanthrolines", *J. Heterocyclic. Chem.*, 18:599, 1981.
Chen et al., "Molecular design and synthesis of a calix[6]crown-based lithium-selective ionophore", *Tetrahedron Lett*, 41:4815-4818, 2000.
Chien et al., "Stereochemistry of Diphenyls. XXXV.[1] The Effect of 3' Substituents on the Rate of Racemization of 2-Nitro-6-carboxy-2'-methoxydiphenyl", *J. Am. Chem. Soc.*, 56:1787-1792, 1934.
Cram et al., "Preorganization—from solvents to spherands", *Angew. Chem. Int. Ed.*, 25:1039-1057, 1986.
Cram et al., "Host-guest complexation. 35. Spherands, the first completely preorganized ligand systems", *J. Am. Chem. Soc.*, 107:3645-3657, 1985.
Ericksen et al., "Chemical composition and distribution of lithium-rich brines in Salar de Uyuni and nearby salars in southwestern Bolivia." *Lithium Needs and Resources*. Pergamon, 355-363, 1978.
Gale et al., "Anion and ion-pair receptor chemistry: highlights from 2000 and 2001", *Coord. Chem. Rev.*, 240:191-221, 2003.
Grote et al., Selective Complexation of $Li^+$ in Water at Neutral pH Using a Self-Assembled Ionophore, *J. Am. Chem. Soc.*, 125:13638-13639, 2003.
Hano et al., "Recovery of lithium from geothermal water by solvent extraction technique", *Solvent Extr. Ion Exc.*, 10:195-206, 1992.
He et al., "Hemispherand-strapped calix [4] pyrrole: an ion-pair receptor for the recognition and extraction of lithium nitrite", *J. Am. Chem. Soc.*, 138:9779-9782, 2016.
Kim and Sessler, "Calix [4] pyrrole-based ion pair receptors", *Acc. Chem. Res.*, 47:2525-2536, 2014.
Kim and Sessler, "Ion pair receptors", *Chem. Soc. Rev.*, 39:3784-3809, 2010.
Kobiro et al., "New class of lithium ion selective crown ethers with bulky decalin subunits", *Coord. Chem. Rev.*, 148:135-149, 1996.
Kollman et al., "Molecular mechanical studies of inclusion of alkali cations into anisole spherands", *J. Am. Chem. Soc.*, 107:2212-2219, 1985.
Lide et al., CRC Handbook, 75th Ed., pp. 12-13, 1995.
Mahoney et al., "Selective Solid-Liquid Extraction of Lithium Halide Salts Using a Ditopic Macrobicyclic Receptor", *Inorg. Chem.*, 43:7617-7621, 2004.

(Continued)

*Primary Examiner* — Kahsay Habte
(74) *Attorney, Agent, or Firm* — Parker Highlander PLLC

(57) ABSTRACT

The present disclosure relates to calixpyrrole compounds and compositions thereof. The calixpyrrole compounds are chemical groups which are located in such a manner so as to be useful for the selective extraction of specific salts. Also provided herein are compositions and methods of use thereof.

19 Claims, 22 Drawing Sheets

(56) References Cited

OTHER PUBLICATIONS

Marcus et al., "Thermodynamics of solvation of ions. Part 5.—Gibbs free energy of hydration at 298.15 K." *J. Chem. Soc. Faraday Trans.*, 87:2995-2999, 1991.

Morita et al., The efficient separation of lithium chloride by acyclic carrier molecules, *Heterocycles*, 70:389-421, 2006.

Paquette and Tae., "Selective Lithium Ion Binding Involving Inositol-Based Tris(spirotetrahydrofuranyl) Ionophores: Formation of a Rod-like Supramolecular Ionic Polymer from a Homoditopic Dimer", *J. Am. Chem. Soc.*, 123:4974-4984, 2001.

Paquette et al., "A belted monofacial ionophore featuring high selectivity for lithium ion complexation", *Angew. Chem. Int. Ed.*, 38:1409-1411, 1999.

PCT International Search Report and Written Opinion issued in International Application No. PCT/US2019/033690, dated Sep. 30, 2019.

Piotrowski and Severin., "A self-assembled, redox-responsive receptor for the selective extraction of LiCl from water", *Proc. Natl. Acad. Sci.USA*, 99:4997-5000, 2002.

Pranolo et al., "Separation of lithium from sodium in chloride solutions using SSX systems with LIX 54 and Cyanex 923", *Hydrometallurgy*, 154:33-39, 2015.

Sharma et al., Synergistic interplay between D2EHPA and TBP towards the extraction of lithium using hollow fiber supported liquid membrane, *Sep. Sci. Technol.*, 51:2242-2254, 2016.

Sonoca et al., "Opportunities to Improve Recycling of Automotive Lithium Ion Batteries", *Procedia CIRP*, 29:752-757, 2015.

Swain et al., "Recovery and recycling of lithium: A review", *Purif. Technol.*, 172:388-403, 2017.

Tsuchiya et al., "Highly Efficient Separation of Lithium Chloride from Seawater", *J. Am. Chem. Soc.*, 124:4936-4937, 2002.

Yoon et al., Benzene-, Pyrrole-, and Furan-Containing Diametrically Strapped Calix[4]pyrroles—An Experimental and Theoretical Study of Hydrogen-Bonding Effects in Chloride Anion Recognition, *Angewandte Chem. Int.*, 47:5038-5042, 2008.

COMPOUNDS FOR THE SELECTIVE SOLID-LIQUID EXTRACTION AND LIQUID-LIQUID EXTRACTION OF LITHIUM CHLORIDE

This application is a national phase application under 35 U.S.C. § 371 of International Application No. PCT/US2019/033690, filed May 23, 2019, which claims the benefit of priority to U.S. Provisional Application No. 62/675,558, filed on May 23, 2018, the entire contents of each of which are hereby incorporated by reference This invention was made with government support under Grant No. DE-FG02-01ER15186 awarded by the Department of Energy. The government has certain rights in the invention.

BACKGROUND OF THE INVENTION

1. Field of the Invention

The present disclosure relates generally to the fields of chemistry, metal extraction, and macrocycles. The present disclosure relates to calixpyrrole compounds and methods for selective extraction of salts such as lithium salts.

2. Description of Related Art

Over the past two decades, the worldwide demand for lithium has increased substantially. This rise is consumption driven by the critical role of lithium in areas as diverse as modern materials, pharmaceuticals, and lithium-ion batteries (LIBs). However, the global lithium reserve is finite. Some estimates have supply from readily accessible lithium resources not being able to meet demand by 2023 (Kara et al., 2015). Compounding the problem is that the global rate of lithium recycling is <1% (Swain, 2017). This provides an incentive to develop new strategies that might allow lithium salts to be isolated from non-traditional supply sources, such as brackish brines, where LiCl is expected to define the dominant lithium form. Both so-called solid-liquid extraction (SLE) and liquid-liquid extraction (LLE) strategies are appealing in this regard. However, such approaches are made challenging by the high lattice (−834 kJ·mol$^{-1}$) and hydration energies (−475 kJ·mol$^{-1}$ for Li$^+$, −340 kJ·mol$^{-1}$ for Cl$^-$) of LiCl (Lide, 1995 and Marcus, 1991)

The design and synthesis of Li$^+$ ionophores dated back to the 1980s, when Cram and his colleagues reported a spherand for recognition of Li$^+$ (Cram et al., 1985 and Cram et al., 1986). Since then, considerable progress has been made in this area. However, most reported systems are cation receptors and require a lipophilic anion (e.g., picrate and perchlorate) to achieve effective Li$^+$ recognition (Chen et al., 2000, Cram et al., 1986, Kobiro et al., 1996, Kollman et al., 1985, Paquette and Tae, 2001, Paquette et al., 1999, and Grote et al., 2003). Therefore, with few exceptions (Morita et al., 2006, Piotrowski and Severin, 2002, and Tsuchiya et al., 2002), unwanted counter anionic components are needed when these systems are applied as extractants for separation of lithium from mixtures (Hano et al., 1992, Pranolo et al., 2015, and Sharma et al., 2016). The use of ion pair receptors (Gale, 2003, Kim and Sessler, 2010, and Kim and Sessler, 2014), small molecules that are capable of binding anions and cations concurrently, may obviate this need. However, the chemistry of ion pair receptors, especially for lithium salt recognition, is not well developed. In 2004, Smith and coworkers reported the SLE extraction of LiCl$_{(s)}$ into CDCl$_3$ with selectivity ratios of 94:4:2 (LiCl:NaCl:KCl) by means of a ditopic ion pair receptor (Mahoney et al., 2004). Impressive as these early results were, further advances are needed. For instance, the Salar de Uyuni in Bolivia, the largest salt flat on earth, contains a large amount of alkali metal salts mainly in their respective chloride forms (i.e., NaCl, KCl and LiCl). However, the lithium content is low (between 80 and 1500 ppm) relative to the high concentrations of competing cations (Ericksen et al., 1978). Direct separation of LiCl from such mixtures, either in brine form or after evaporation to a solid salt mixture or from a liquid to another liquid composition, remains an unmet challenge.

SUMMARY OF THE INVENTION

In some aspects, the present disclosure provides compounds

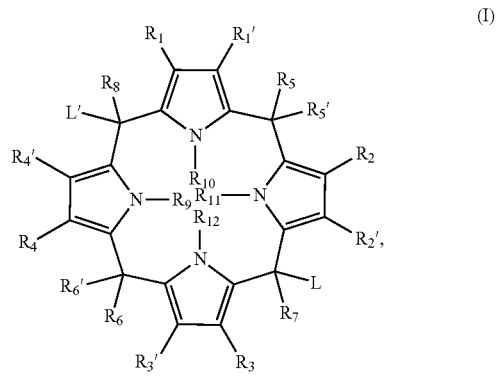

(I)

wherein:
R$_1$, R$_1$', R$_2$, R$_2$', R$_3$, R$_3$', R$_4$, and R$_4$' are each independently hydrogen, hydroxy, amino, cyano, or halo; or alkyl$_{(C≤6)}$, alkenyl$_{(C≤6)}$, alkynyl$_{(C≤6)}$, acyloxy$_{(C≤6)}$, alkoxy$_{(C≤6)}$, alkylamino$_{(C≤6)}$, dialkylamino$_{(C≤12)}$, amido$_{(C≤6)}$, or a substituted version of any of these groups; or
one of these groups is attached to a solid support or a fluorophore;
R$_5$, R$_5$', R$_6$, R$_6$', R$_7$, and R$_8$ are each independently hydrogen or alkyl$_{(C≤12)}$, cycloalkyl$_{(C≤12)}$, cycloalkenyl$_{(C≤12)}$, alkenyl$_{(C≤12)}$, alkynyl$_{(C≤12)}$, aryl$_{(C≤12)}$, heteroalkyl$_{(C≤12)}$, heterocycloalkyl$_{(C≤12)}$, alkoxy$_{(C≤12)}$, alkylamino$_{(C≤12)}$, dialkylamino$_{(C≤18)}$, amido$_{(C≤12)}$, or a substituted version of any of these groups; or one of these groups is attached to a solid support or a fluorophore;
R$_9$, R$_{10}$, R$_{11}$, and R$_{12}$ are hydrogen, alkyl$_{(C≤6)}$, or substituted alkyl$_{(C≤6)}$;
L and L' are taken together and form a group of the formula:

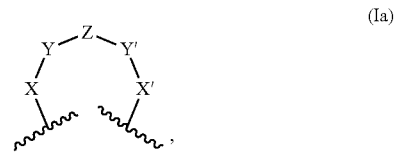

(Ia)

wherein:
X and X' are each independently alkanediyl$_{(C≤8)}$, cycloalkanediyl$_{(C≤8)}$, alkenediyl$_{(C≤8)}$, alkynediyl$_{(C≤8)}$, arenediyl$_{(C≤8)}$, or a substituted version of any of these groups;

Y and Y' are each independently —O—, —C(O)—, —C(O)O—, —S(O)—, —S(O)$_2$O—, —C(O)NR$_a$—, or —S(O)$_2$NR$_b$—, wherein:
R$_a$ and R$_b$ are each independently hydrogen, alkyl$_{(C≤6)}$, or substituted alkyl$_{(C≤6)}$; or one or more of these groups is attached to a solid support or a fluorophore;
Z is a group of the formula:

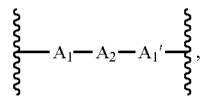
(Ib)

wherein:
A$_1$ and A$_1$' are each independently arenediyl$_{(C≤8)}$, substituted arenediyl$_{(C≤8)}$, heteroarenediyl$_{(C≤8)}$ or substituted heteroarenediyl$_{(C≤8)}$; and
A$_2$ is heteroarenediyl$_{(C≤8)}$ or substituted heteroarenediyl$_{(C≤8)}$; or
Z is arenediyl$_{(C≤24)}$, substituted arenediyl$_{(C≤24)}$, heteroarenediyl$_{(C≤24)}$, or substituted heteroarenediyl$_{(C≤24)}$, wherein the group comprises at least 3 fused rings;
or a salt thereof.

In some embodiments, the compounds are further defined as:

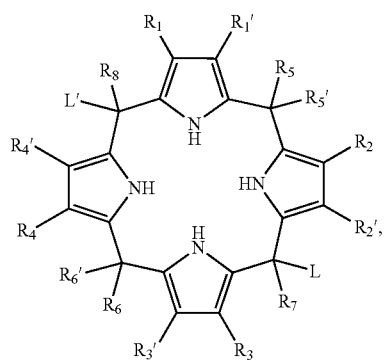
(II)

wherein:
R$_1$, R$_1$', R$_2$, R$_2$', R$_3$, R$_3$', R$_4$, and R$_4$' are each independently hydrogen, hydroxy, amino, cyano, or halo; or alkyl$_{(C≤6)}$, alkenyl$_{(C≤6)}$, alkynyl$_{(C≤6)}$, acyloxy$_{(C≤6)}$, alkoxy$_{(C≤6)}$, alkylamino$_{(C≤6)}$, dialkylamino$_{(C≤12)}$, amido$_{(C≤6)}$, or a substituted version of any of these groups;
R$_5$, R$_5$', R$_6$, R$_6$', R$_7$, and R$_8$ are each independently hydrogen or alkyl$_{(C≤6)}$, alkenyl$_{(C≤6)}$, alkynyl$_{(C≤6)}$, or a substituted version of any of these groups;
L and L' are taken together and form a group of the formula:

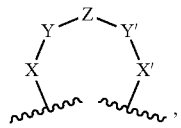
(Ia)

wherein:
X and X' are each independently alkanediyl$_{(C≤8)}$, alkenediyl$_{(C≤8)}$, alkynediyl$_{(C≤8)}$, or a substituted version of any of these groups;
Y and Y' are each independently —C(O)—, —C(O)O—, —S(O)—, —S(O)$_2$O—, —C(O)NR$_a$—, or —S(O)$_2$NR$_b$—, wherein:
R$_a$ and R$_b$ are each independently hydrogen, alkyl$_{(C≤6)}$, or substituted alkyl$_{(C≤6)}$;
Z is a group of the formula:

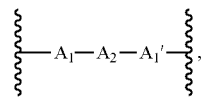
(Ib)

wherein:
A$_1$ and A$_1$' are each independently arenediyl$_{(C≤8)}$, substituted arenediyl$_{(C≤8)}$, heteroarenediyl$_{(C≤8)}$ or substituted heteroarenediyl$_{(C≤8)}$; and
A$_2$ is heteroarenediyl$_{(C≤8)}$ or substituted heteroarenediyl$_{(C≤8)}$; or
Z is arenediyl$_{(C≤24)}$, substituted arenediyl$_{(C≤24)}$, heteroarenediyl$_{(C≤24)}$, or substituted heteroarenediyl$_{(C≤24)}$, wherein the group comprises at least 3 fused rings;
or a salt thereof.

In some embodiments, the compounds are further defined:

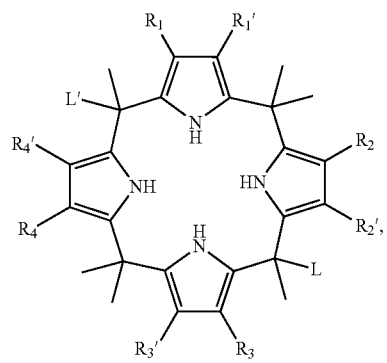
(III)

wherein:
R$_1$, R$_1$', R$_2$, R$_2$', R$_3$, R$_3$', R$_4$, and R$_4$' are each independently hydrogen, hydroxy, amino, cyano, or halo; or alkyl$_{(C≤6)}$, alkenyl$_{(C≤6)}$, alkynyl$_{(C≤6)}$, acyloxy$_{(C≤6)}$, alkoxy$_{(C≤6)}$, alkylamino$_{(C≤6)}$, dialkylamino$_{(C≤12)}$, amido$_{(C≤6)}$, or a substituted version of any of these groups;
L and L' are taken together and form a group of the formula:

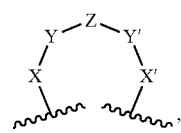
(Ia)

wherein:
X and X' are each independently alkanediyl$_{(C\leq 8)}$, alkenediyl$_{(C\leq 8)}$, alkynediyl$_{(C\leq 8)}$, or a substituted version of any of these groups;
Y and Y' are each independently —C(O)—, —C(O)O—, —S(O)—, —S(O)$_2$O—, —C(O)NR$_a$—, or —S(O)$_2$NR$_b$—, wherein:
R$_a$ and R$_b$ are each independently hydrogen, alkyl$_{(C\leq 6)}$, or substituted alkyl$_{(C\leq 6)}$;
Z is a group of the formula:

$$\text{\textbraceleft}\!\!-\!\!A_1\!-\!A_2\!-\!A_1'\!\!-\!\!\text{\textbraceright} \quad (Ib)$$

wherein:
A$_1$ and A$_1$' are each independently arenediyl$_{(C\leq 8)}$, substituted arenediyl$_{(C\leq 8)}$, heteroarenediyl$_{(C\leq 8)}$ or substituted heteroarenediyl$_{(C\leq 8)}$; and
A$_2$ is heteroarenediyl$_{(C\leq 8)}$ or substituted heteroarenediyl$_{(C\leq 8)}$; or
Z is arenediyl$_{(C\leq 24)}$, substituted arenediyl$_{(C\leq 24)}$, heteroarenediyl$_{(C\leq 24)}$, or substituted heteroarenediyl$_{(C\leq 24)}$, wherein the group comprises at least 3 fused rings;
or a salt thereof.
In some embodiments, the compounds are further defined:

(IV)

wherein:
L and L' are taken together and form a group of the formula:

(Ia)

wherein:
X and X' are each independently alkanediyl$_{(C\leq 8)}$, alkenediyl$_{(C\leq 8)}$, alkynediyl$_{(C\leq 8)}$, or a substituted version of any of these groups;
Y and Y' are each independently —C(O)—, —C(O)O—, —S(O)—, —S(O)$_2$O—, —C(O)NR$_a$—, or —S(O)$_2$NR$_b$—, wherein:
R$_a$ and R$_b$ are each independently hydrogen, alkyl$_{(C\leq 6)}$, or substituted alkyl$_{(C\leq 6)}$;
Z is a group of the formula:

$$\text{\textbraceleft}\!\!-\!\!A_1\!-\!A_2\!-\!A_1'\!\!-\!\!\text{\textbraceright} \quad (Ib)$$

wherein:
A$_1$ and A$_1$' are each independently arenediyl$_{(C\leq 8)}$, substituted arenediyl$_{(C\leq 8)}$, heteroarenediyl$_{(C\leq 8)}$ or substituted heteroarenediyl$_{(C\leq 8)}$; and A₂ is heteroarenediyl$_{(C≤8)}$ or substituted heteroarenediyl$_{(C≤8)}$;
or a salt thereof.

In some embodiments, the compound is further defined:

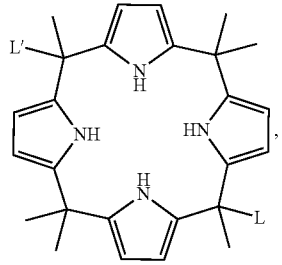

(IV)

wherein:
L and L' are taken together and form a group of the formula:

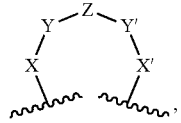

(Ia)

wherein:
X and X' are each independently alkanediyl$_{(C≤8)}$, alkenediyl$_{(C≤8)}$, alkynediyl$_{(C≤8)}$, or a substituted version of any of these groups;
Y and Y' are each independently —C(O)—, —C(O)O—, —S(O)—, —S(O)₂O—, —C(O)NR$_a$—, or —S(O)₂NR$_b$—, wherein:
R$_a$ and R$_b$ are each independently hydrogen, alkyl$_{(C≤6)}$, or substituted alkyl$_{(C≤6)}$; and
Z is arenediyl$_{(C≤24)}$, substituted arenediyl$_{(C≤24)}$, heteroarenediyl$_{(C≤24)}$, or substituted heteroarenediyl$_{(C≤24)}$, wherein the group comprises at least 3 fused rings;
or a salt thereof.

In some embodiments, X and X' are both the same such as when X and X' are both alkanediyl$_{(C≤8)}$ or substituted alkanediyl$_{(C≤8)}$. In some embodiments, X and X' are both alkanediyl$_{(C≤8)}$. In some embodiments, X and X' are both alkanediyl$_{(C≤4)}$ such as both ethanediyl or propanediyl. In some embodiments, Y and Y' are both the same such as when Y and Y' are both —C(O)O— or —C(O)NR$_a$—. In some embodiments, Y and Y' are both —C(O)NR$_a$—. In some embodiments, R$_a$ is alkyl$_{(C≤6)}$, or substituted alkyl$_{(C≤6)}$. In some embodiments, R$_a$ is alkyl$_{(C≤6)}$. In other embodiments, Y and Y' are both —C(O)O—.

In some embodiments, A₁ and A₁' are both the same such as when A₁ and A₁' are both arenediyl$_{(C≤8)}$ or substituted arenediyl$_{(C≤8)}$. In some embodiments, A₁ and A₁' are both substituted arenediyl$_{(C≤8)}$. In some embodiments, A₁ and A₁' are both methoxybenzenediyl such as both are 1-methoxybenzene-2,6-diyl. In some embodiments, A₂ is heteroarenediyl$_{(C≤8)}$. In some embodiments, A₂ is pyridinediyl such as pyridine-2,6-diyl.

In some embodiments, Z is substituted arenediyl$_{(C≤24)}$, heteroarenediyl$_{(C≤24)}$, or substituted heteroarenediyl$_{(C≤24)}$, wherein the group comprises at least 3 fused rings. In some embodiments, Z is heteroarenediyl$_{(C≤24)}$ or substituted heteroarenediyl$_{(C≤24)}$, wherein the group comprises at least 3 fused rings. In some embodiments, Z is heteroarenediyl$_{(C≤24)}$, wherein the group comprises at least 3 fused rings such as a heteroarenediyl$_{(C≤24)}$ wherein the group comprises 3 fused rings. In some embodiments, Z is heteroarenediyl$_{(C≤18)}$, wherein the group comprises 3 fused rings. In some embodiments, Z is heteroarenediyl$_{(C≤18)}$, wherein the group comprises 3 fused rings and contains at least two nitrogen atoms such as when the heteroarenediyl$_{(C≤18)}$, wherein the group comprises 3 fused rings and contains two nitrogen atoms. In some embodiments, Z is phenanthrolinediyl such as phenanthroline-2,9-diyl.

In some embodiments, the compounds are further defined:

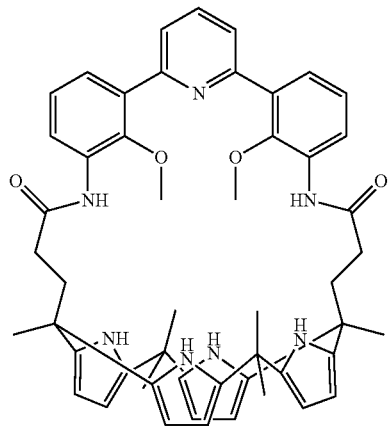

or

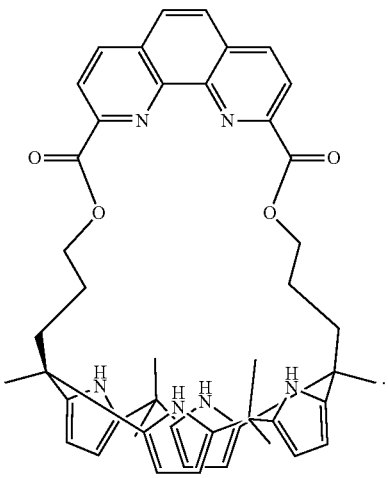

In yet another aspect, the present disclosure provides compositions comprising a compound described herein and a salt. In some embodiments, the salt comprises an alkali metal cation. In some embodiments, the alkali metal cation is lithium(I). In some embodiments, the salt comprises a halogen anion such as chloride. In some embodiments, the salt is lithium(I) chloride. In some embodiments, the compound is defined as:

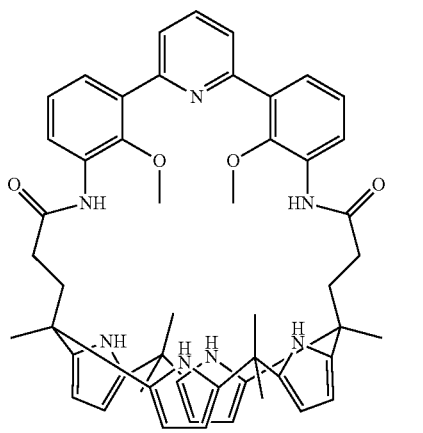

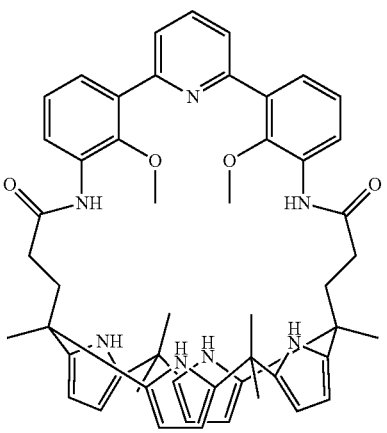

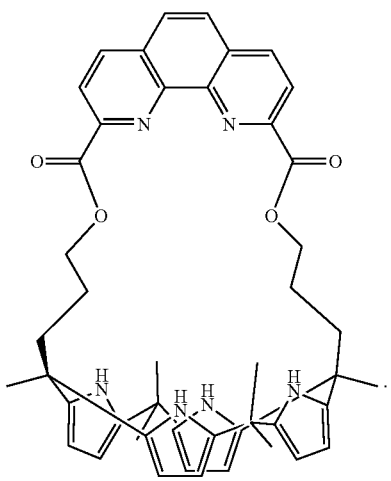

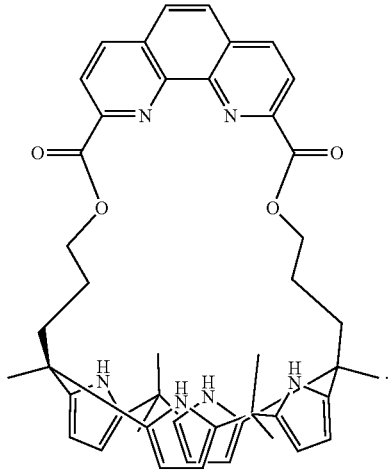

In still yet another aspect, the present disclosure provides methods of sequestering a target compound in a first solution comprising contacting the first solution with a compound described herein. In some embodiments, the target compound is a salt. In some embodiments, the salt comprises an alkali metal cation such as lithium(I). In some embodiments, the salt comprises a halogen anion such as chloride. In some embodiments, the salt is lithium(I) chloride. In some embodiments, the first solution is an aqueous solution. In some embodiments, the compound is dissolved in a solvent prior to contacting the first solution. In some embodiments, the solvent is an organic solvent such as nitrobenzene. In other embodiments, the organic solvent is chloroform. In some embodiments, the target compound is separated from first solution. In some embodiments, the compound is further defined as:

In still yet another aspect, the present disclosure provides methods of carrying out a liquid-liquid extraction of a salt from a first solution to form a complex with a compound described herein, wherein the compound is dissolved in a liquid.

In yet another aspect, the present disclosure provides methods of carrying out a solid-liquid extraction of a salt from a solid to form a complex with a compound described herein, wherein the compound is dissolved in a liquid.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 33B) NaCl; (FIG. 33C) KCl; (FIG. 33D) extracted nitrobenzene solutions of 2 after contacting with a mixture of NaCl and KCl containing 10% of LiCl (mass content); (FIG. 33E) analogous experiments where the LiCl content was 1% by mass; (FIG. 33F) the extracted solution obtained using receptor 3 as the extractant and a mixture of NaCl and KCl containing 200 ppm of LiCl (mass content) as the source phase.

(FIG. 34B) the extracted nitrobenzene solutions of 2 after contacting with a mixture of LiCl, NaCl and KCl (100:100:100, molar ratio).

DESCRIPTION OF ILLUSTRATIVE EMBODIMENTS

Figures 1A, 1B:
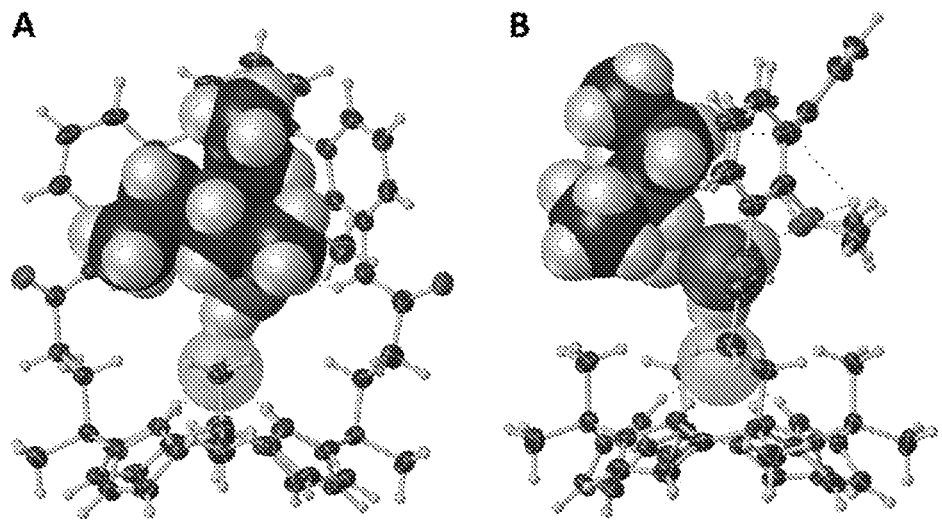
FIGS. 1A & 1B shows front (FIG. 1A) and side (FIG. 1B) views of an X-ray diffraction structure of 2·TEA·HF complex obtained from single crystals grown by subjecting a solution of 2·Et₃N·HF in CH₂Cl₂/methanol to slow evaporation. Et₃NH⁺, H₂O and F⁻ are shown as space-filling models. Displacement ellipsoids are scaled to the 50% probability level. Other solvent molecules have been removed for clarity.

The present disclosure describes calixpyrrole compounds and compositions and methods of use thereof. One non-limiting example of the use of these compounds is in the selective extraction of LiCl. The present disclosure provides the synthesis and analysis of calix[4]pyrrole-based ion pair receptors, such as 2 and 3, that allow LiCl to be captured selectively under SLE conditions. Furthermore, in some aspects, system 3 also permits the selective LLE extraction of LiCl into chloroform from an aqueous source phase. Additionally, the compositions herein may have the advantage of separating lithium salts such as lithium chloride dissolved in an aqueous solution from other halide salts into an organic solvent. Furthermore, systems 2 and 3 are also capable of stabilizing a LiCl complex in the solid state as a receptor system without an intervening water molecule between the Li$^+$ cation and Cl$^-$ anion.

A. Calixpyrroles of the Present Disclosure

The compounds of the present invention (also referred to as "compounds of the present disclosure") are shown, for example, above, in the summary of the invention section, and in the claims below. They may be made using the synthetic methods outlined in the Examples section. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure*, (2013), which is incorporated by reference herein. In addition, the synthetic methods may be further modified and optimized for preparative, pilot- or large-scale production, either batch or continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

The calixpyrroles of the present disclosure may include further modifications to allow substitutions on the calixpyrrole core. Such modified calixpyrroles include those described in U.S. Pat. Nos. 6,262,257, 6,984,734, 7,041,819, and 7,122,572 as well as U.S. Patent Application Publication No. 2010/0129308 and U.S. 2010/0120958, the entire contents of which are hereby incorporated by reference. The compounds described herein include attachment of the instant calixpyrroles to a solid support or a polymer to better achieve separation of the desired metal ions. Such systems are described in U.S. Pat. No. 8,802,074, the entire contents of which are hereby incorporated by reference.

Compounds of the present invention may contain one or more asymmetrically-substituted carbon or nitrogen atoms and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained.

The chiral centers of the compounds of the present invention can have the S or the R configuration. In some embodiments, the present compounds may contain two or more atoms which have a defined stereochemical orientation.

Chemical formulas used to represent compounds of the present invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

B. Definitions

When used in the context of a chemical group: "hydrogen" means H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanyl" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "===" represents a single bond or a double bond. Thus, the formula

covers, for example,

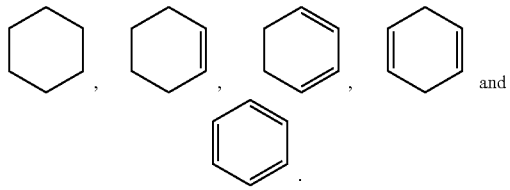

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "～", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◄" means a single bond where the group attached to the thick end of the wedge is "out of the page." The symbol "⫼⫼⫼" means a single bond where the group attached to the thick end of the wedge is "into the page". The symbol "～" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

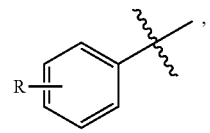

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

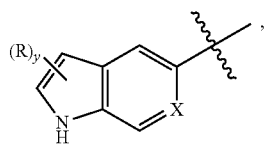

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C≤8)}$", "cycloalkanediyl$_{(C≤8)}$", "heteroaryl$_{(C≤8)}$", and "acyl$_{(C≤8)}$" is one, the minimum number of carbon atoms in the groups "alkenyl$_{(C≤8)}$", "alkynyl$_{(C≤8)}$", and "heterocycloalkyl$_{(C≤8)}$" is two, the minimum number of carbon atoms in the group "cycloalkyl$_{(C≤8)}$" is three, and the minimum number of carbon atoms in the groups "aryl$_{(C≤8)}$" and "arenediyl$_{(C≤8)}$" is six. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the class of compounds having the formula H—R, wherein R is cycloalkyl as this term is defined above. When any of these terms are used with the "substituted" modifier one or more hydrogen atom has been independently replaced by —OH, —F, —Cl, —Br, —I, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula HR, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "cycloalkenyl" refers to a monovalent saturated aliphatic group with a carbon atom as the point of attachment, said carbon atom forming part of one or more non-aromatic ring structures, one or more carbon-carbon double bonds provided the group is not aromatic, no carbon-carbon triple bonds, and no atoms other than carbon and hydrogen. Non-limiting examples include: cyclopropenyl, cyclobutenyl, cyclopentenyl, or cyclohexenyl. As used herein, the term does not preclude the presence of one or more alkyl groups (carbon number limitation permitting) attached to a carbon atom of the non-aromatic ring structure. A "cycloalkene" refers to the class of compounds having the formula HR, wherein R is cycloalkenyl as this term is defined above. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. The term "alkynediyl" when used without the "substituted" modifier refers to a divalent unsaturated aliphatic group, with two carbon atoms as points of attachment, a linear or branched acyclic structure, at least one nonaromatic carbon-carbon triple bond, no carbon-carbon double bonds, and no atoms other than carbon and hydrogen. The groups —C≡CCH$_2$—, and —CH$_2$C≡CCH$_2$— re non-limiting examples of alkynediyl groups. It is noted that while the alkynediyl group is aliphatic, once connected at both ends, this group is not precluded from forming part of an aromatic structure. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl (e.g., 4-phenylphenyl). The term "arenediyl" when used without the "substituted" modifier refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

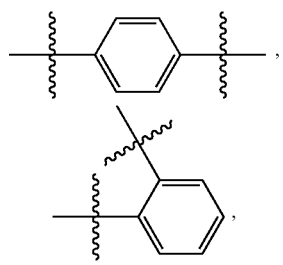

-continued

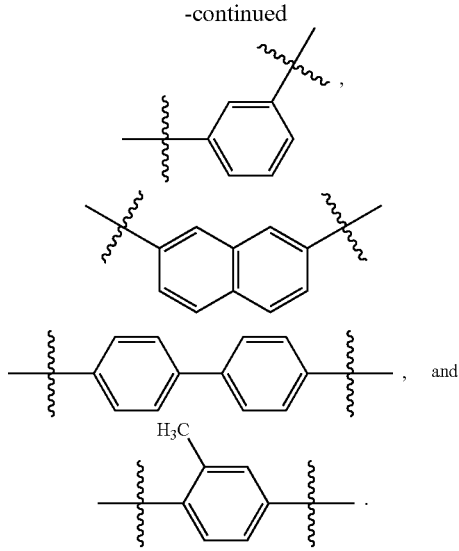

and

An "arene" refers to the class of compounds having the formula HR, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures, each with three to eight ring atoms, wherein at least one of the ring atoms of the aromatic ring structure(s) is nitrogen, oxygen or sulfur, and wherein the heteroaryl group consists of no atoms other than carbon, hydrogen, aromatic nitrogen, aromatic oxygen and aromatic sulfur. If more than one ring is present, the rings are fused; however, the term heteroaryl does not preclude the presence of one or more alkyl or aryl groups (carbon number limitation permitting) attached to one or more ring atoms. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to a divalent aromatic group, with two aromatic carbon atoms, two aromatic nitrogen atoms, or one aromatic carbon atom and one aromatic nitrogen atom as the two points of attachment, said atoms forming part of one or more aromatic ring structures, each with three to eight ring atoms, wherein at least one of the ring atoms of the aromatic ring structure(s) is nitrogen, oxygen or sulfur, and wherein the divalent group consists of no atoms other than carbon, hydrogen, aromatic nitrogen, aromatic oxygen and aromatic sulfur. If more than one ring is present, the rings be fused; however, the term heteroarenediyl does not preclude the presence of one or more alkyl or aryl groups (carbon number limitation permitting) attached to one or more ring atoms. Non-limiting examples of heteroarenediyl groups include:

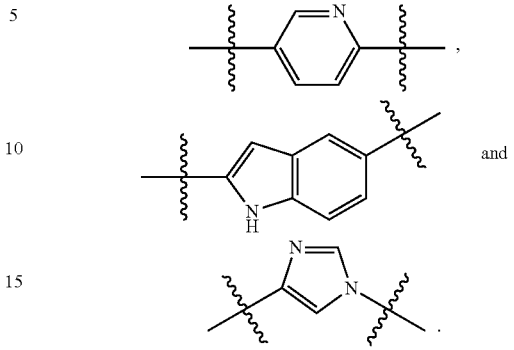

and

A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heterocycloalkyl" refers to a monovalent non-aromatic group with a carbon atom or nitrogen atom as the point of attachment, said carbon atom or nitrogen atom forming part of one or more non-aromatic ring structures, each with three to eight ring atoms, wherein at least one of the ring atoms of the non-aromatic ring structure(s) is nitrogen, oxygen or sulfur, and wherein the heterocycloalkyl group consists of no atoms other than carbon, hydrogen, nitrogen, oxygen and sulfur. If more than one ring is present, the rings are fused. As used herein, the term does not preclude the presence of one or more alkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H$_5$, and —C(O)C$_6$H$_4$CH$_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), or —OC(CH$_3$)$_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group NRR', in which R and R' can be the same or different alkyl groups. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", and "alkoxyamino" when used without the "substituted" modifier, refers to groups, defined as —NHR, in which R is cycloalkyl, alkenyl, alkynyl, aryl, aralkyl, heteroaryl, heterocycloalkyl, and alkoxy, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. When any of these terms is used with the "substituted" modifier, one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects or patients.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

As used herein, the term "ligand" references to a chemical group which coordinates to a metal center through a bond. The bond between the ligand and the metal center in some cases is either an ionic or a coordination bond. A ligand can be monovalent, divalent, trivalent or have a greater valency. In some cases, a ligand may be negatively charged. Some exemplary examples of ligands include, but are not limited to, halide (F$^-$, Cl$^-$, Br$^-$, or I$^-$), a carbonate (CO$_3^{2-}$), bicarbonate (HCO$_3^-$), hydroxide ($^-$OH), perchlorate (ClO$_4^-$), nitrate (NO$_3^-$), sulfate (SO$_4^{2-}$), acetate (CH$_3$CO$_2^-$), trifluoroacetate (CF$_3$CO$_2^-$), acetylacetonate (CH$_3$COCHCOCH$_3^-$), trifluorosulfonate (CF$_3$SO$_2^-$), phosphate (PO$_4^{3-}$), oxalate, ascorbate, or gluconate. A ligand could also be a neutral species that contains a lone pair of electrons. Some examples of neutral ligands include but are not limited to aqua (H$_2$O) or ammonia (NH$_3$). Additionally, a neutral ligand can include groups such as an alkylamine or a dialkylamine.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1: Results and Discussion

Recently, an ion pair receptor (1, He et al., 2016) was shown to permit the extraction of $LiNO_2$(aq) into an organic phase (Scheme 1). However, neither this system nor Smith's proved effective for LiCl under LLE conditions (Mahoney et al., 2004). This failure may reflect an inability to stabilize LiCl complexes that are free of a bridging water molecule between the co-bound charge dense $Cl^-$ anion and $Li^+$ cation. It was envisioned that the effectiveness and selectivity of ion pair binding might be enhanced if direct contact between co-bound ions could be enforced by use of receptors containing smaller internal cavities since it might maximize the Coulombic attraction within the complex. To test this hypothesis within the context of LLE and SLE, ditopic ion-pair receptors 2 and 3 were prepared. These new systems were fully characterized by standard spectroscopic means, as well as by X-ray diffraction analysis (Schemes 1-2 and FIGS. 1 & 2).

Scheme 1. Chemical structures of receptors 1-3.

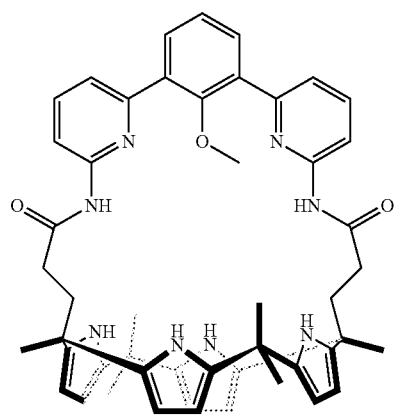

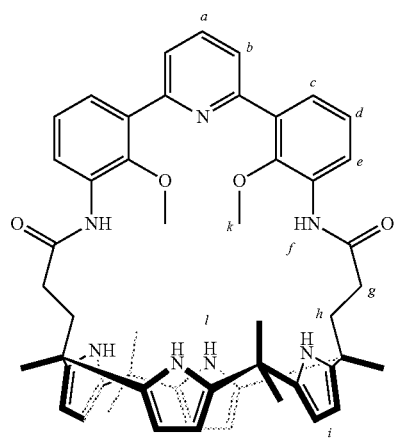

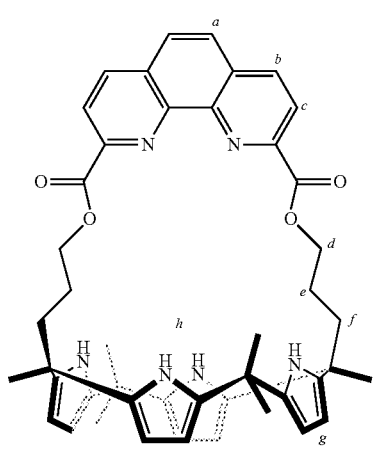

Figures 3A, 3B:
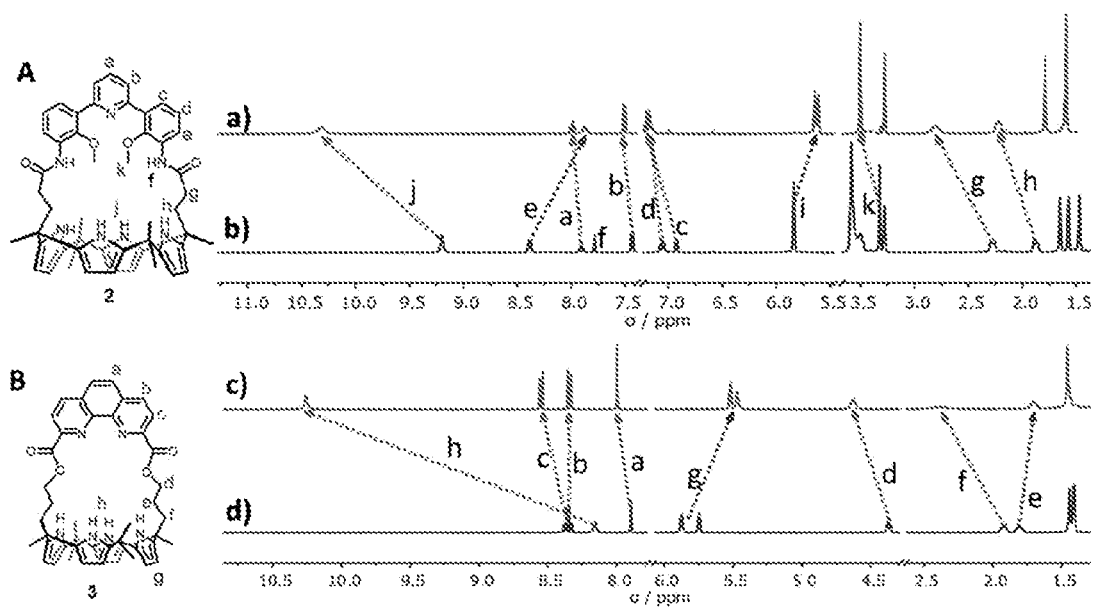
FIGS. 3A & 3B show a partial ¹H NMR spectra of (FIG. 3A) a 4.0 mM solution of (a) 2+excess LiCl, (b) 2 only and (FIG. 3B) a 3.0 mM solution of (c) 3+excess LiCl, (d) 3 only in CDCl₃/CD₃OD (9:1, v/v). The ¹H NMR spectra were recorded after 2 and 3 in the solvent mixture were treated with excess LiCl(s) and allowed to equilibrate for 60 minutes. The dashed lines have been added to aid in visualization.

As a first step toward testing whether 2 and 3 would act as ion pair receptors, their ability to bind LiCl salts was probed via $^1$H NMR spectroscopy in a mixture of $CDCl_3$/$CD_3OD$ (9:1, v/v). As is shown in FIGS. 3A & 3B, significant chemical shift changes were observed when these two receptors were treated with excess $LiCl_{(s)}$ and allowed to equilibrate for 60 minutes. Specifically, upon exposure to excess LiCl in this way, all aromatic hydrogen atoms signals (denoted a, b, c, and d), along with the aliphatic proton signals denoted k, g, and h of receptor 2 underwent downfield shifts. Similarly, in the case of receptor 3, the phenanthroline protons a, b, and c and the aliphatic protons d and f shifted to lower field in the presence of excess LiCl. Such observations are consistent with the Li$^+$ cations being bound to the hemispherand and phenanthroline subunits in the case of 2 and 3, respectively. Evidence for interactions between the calix[4]pyrrole subunits present in 2 and 3 and the chloride anions of LiCl came from the large downfield shifts observed for the pyrrolic. NH protons (j for 2 and h for 3) and the slight upfield shifts seen for the pyrrolic CH protons (i for 2 and g for 3).

Figures 4A, 4B:
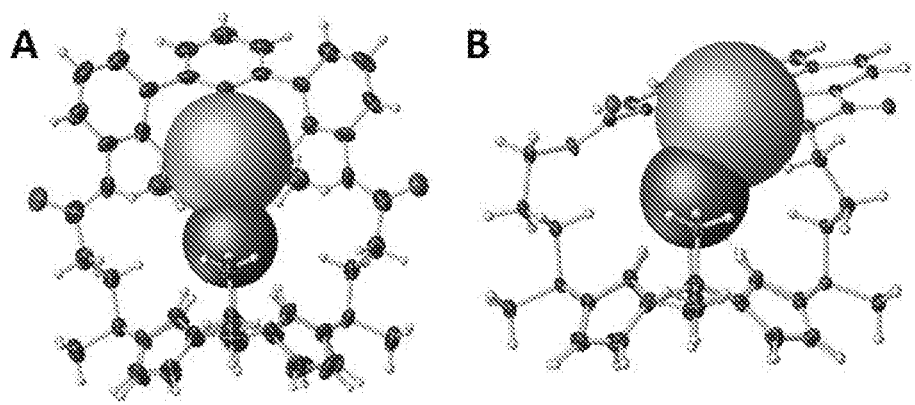
FIGS. 4A & 4B show a single-crystal structures of (FIG. 4A) 2·LiCl and (FIG. 4B) 3·LiCl. The Li⁺ and Cl⁻ ions are shown in space-filling form. Displacement ellipsoids are scaled to the 50% probability level. Solvent molecules are omitted for clarity.
Figures 5A, 5B, 5C, 5D:
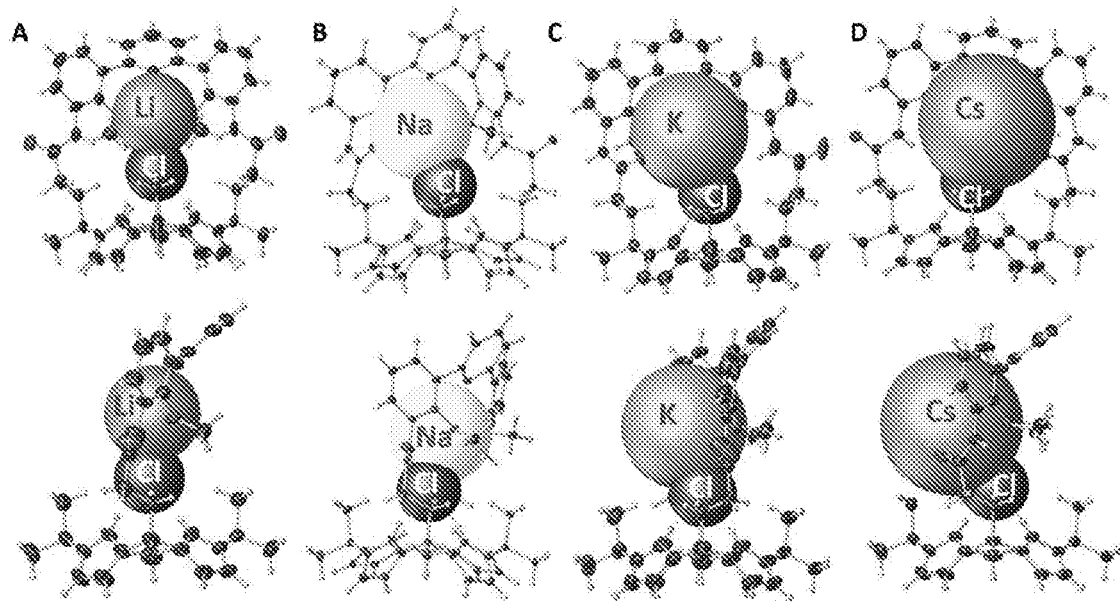
FIGS. 5A-5D show front (top) and side views (bottom) of single crystal structures of complexes of receptor 2 with (FIG. 5A) LiCl, (FIG. 5B) NaCl, (FIG. 5C) KCl, and (FIG. 5D) CsCl. Inorganic ion pairs are shown using space-filling models. Displacement ellipsoids are scaled to the 50% probability level. Solvent molecules have been removed for clarity.
Figure 6:
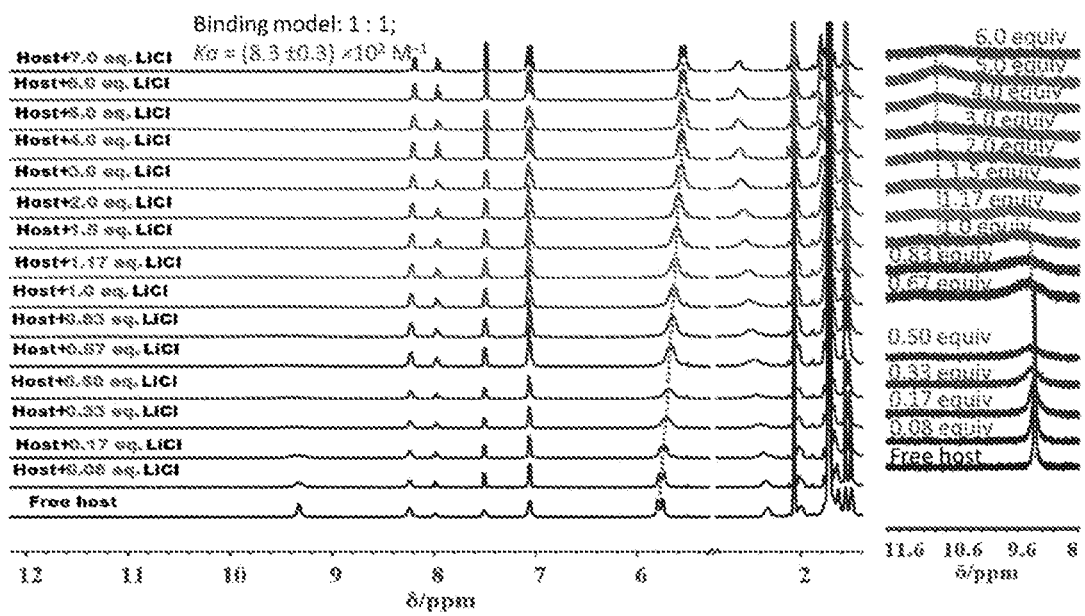
FIG. 6 shows an ¹H NMR spectroscopic titration of receptor 2 with LiCl in a mixed solvent consisting of THF-d₈/D₂O (9/1, v/v). The concentration of 2 was 4.0 mM.
Figure 7:
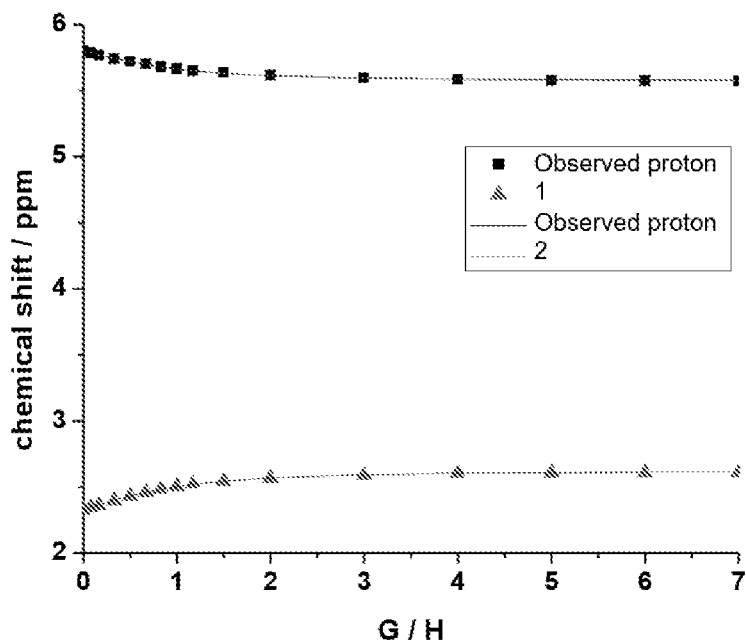
FIG. 7 shows a binding curve obtained by fitting the chemical shift change of the indicated proton signals against [LiCl]. $K_a=(8.3\pm0.3)\times10^2$ M⁻¹.
Figure 8:
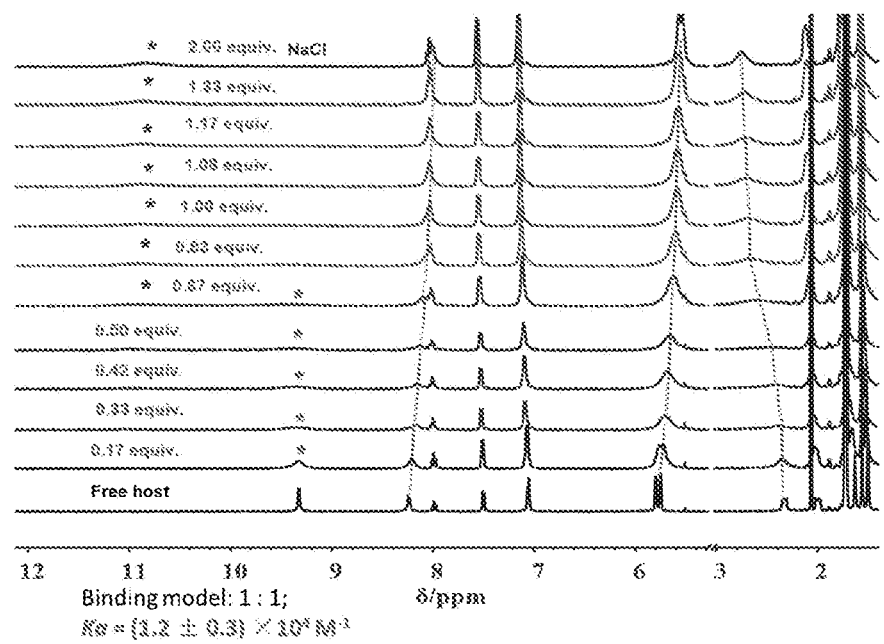
FIG. 8 shows an ¹H NMR spectroscopic titration of receptor 2 with NaCl in a mixed solvent consisting of THF-d₈/D₂O (9/1, v/v). The concentration of 2 was 4.0 mM.
Figure 9:
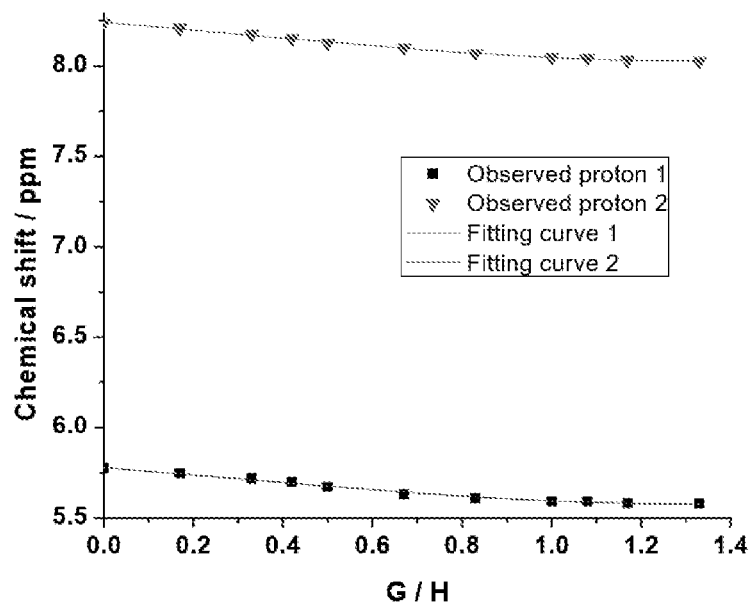
FIG. 9 shows a binding curve obtained by fitting the chemical shift change of the indicated proton signals against [NaCl]. $K_a=(1.2\pm0.3)\times10^4$ M⁻¹.
Figure 10:
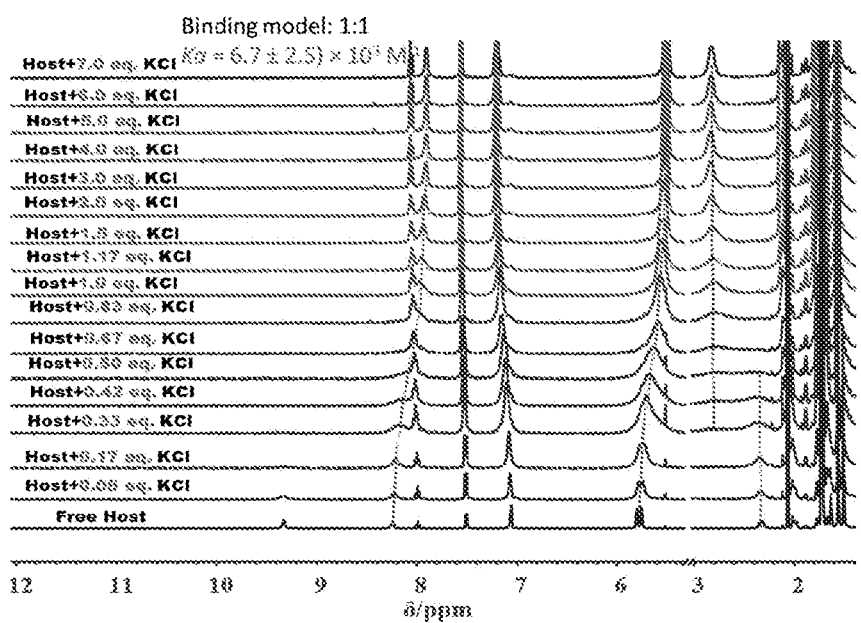
FIG. 10 shows an ¹H NMR spectroscopic titration of receptor 2 with KCl in a mixed solvent consisting of THF-d₈/D₂O (9/1, v/v). The concentration of 2 was 4.0 mM.
Figure 11:
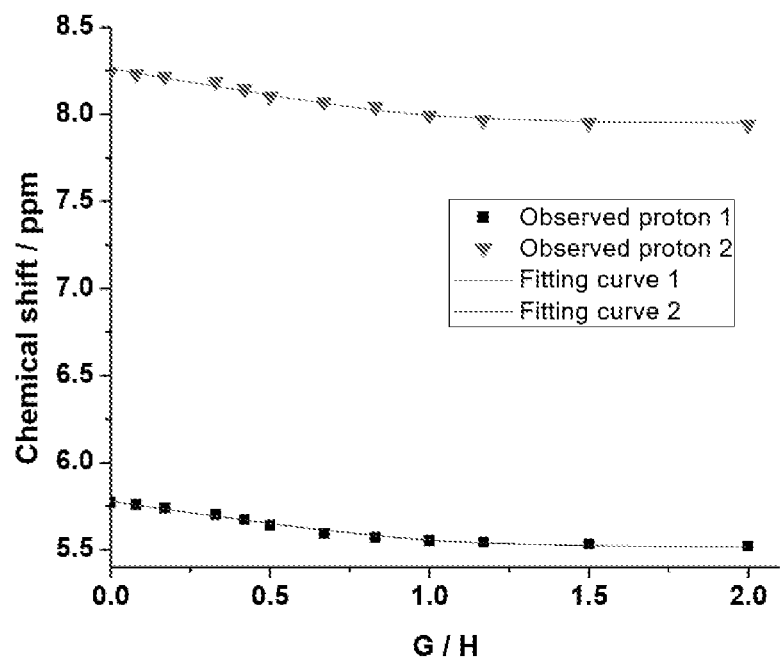
FIG. 11 shows the binding curve obtained by fitting the chemical shift change of the indicated proton signals against [KCl]. $K_a=(6.7\pm2.5)\times10^3$ M⁻¹.
Figure 12:
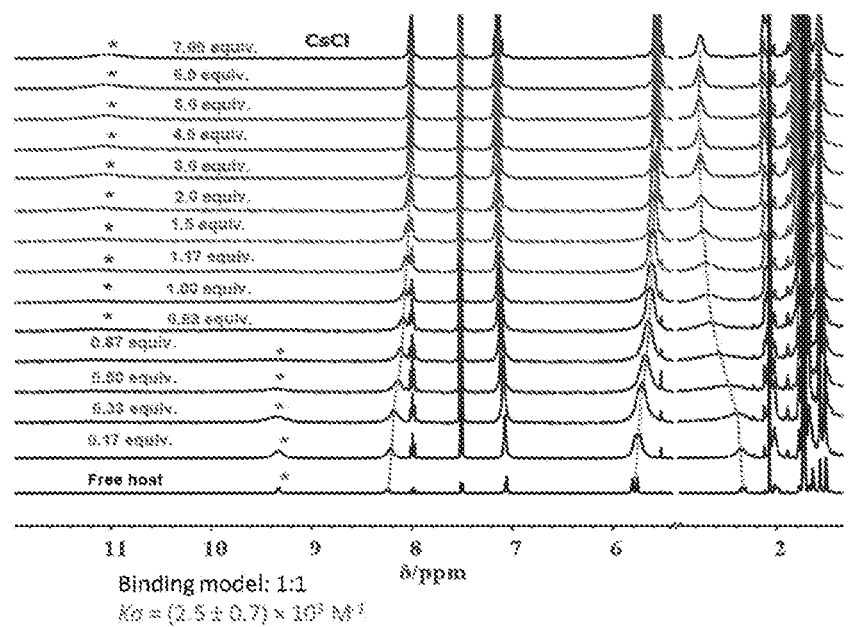
FIG. 12 shows an ¹H NMR spectroscopic titration of receptor 2 with CsCl in a mixed solvent consisting of THF-d₈/D₂O (9/1, v/v). The concentration of 2 was 4.0 mM.
Figure 13:
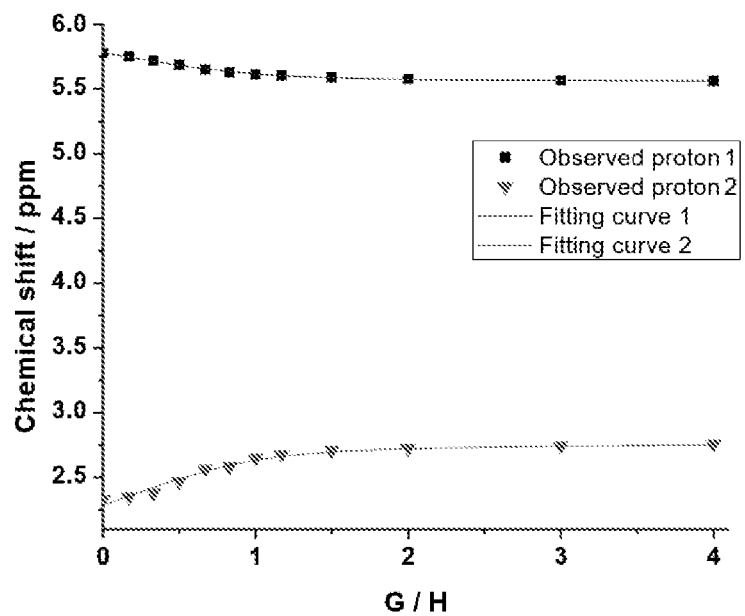
FIG. 13 shows the binding curve obtained by fitting the chemical shift change of the proton signals against [CsCl]. $K_a=(2.5\pm0.7)\times10^3$ M⁻¹.
Figure 14:
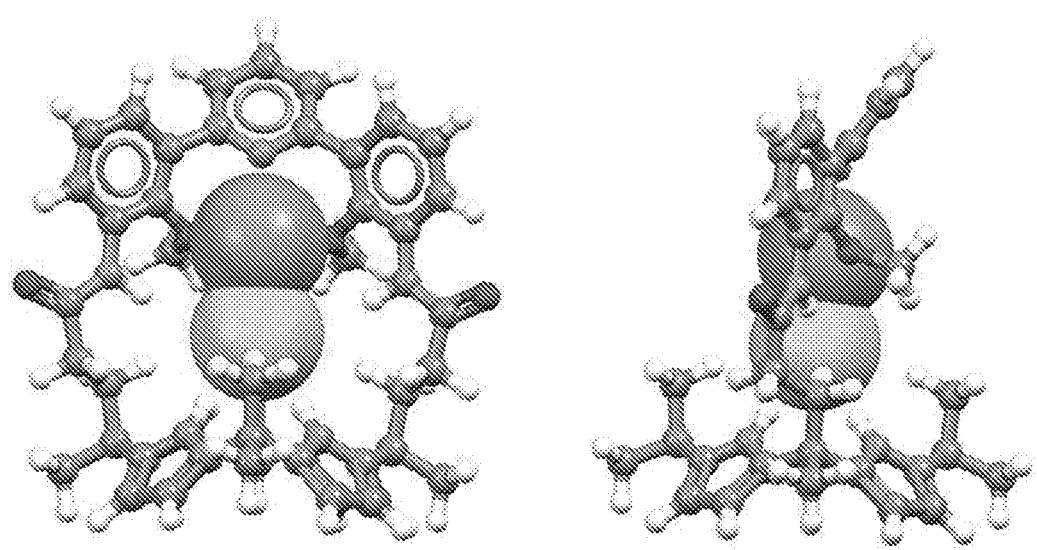
FIG. 14 shows front (left) and side (right) views of the DFT optimized structure of the LiCl complex of receptor 2.
Figure 15:
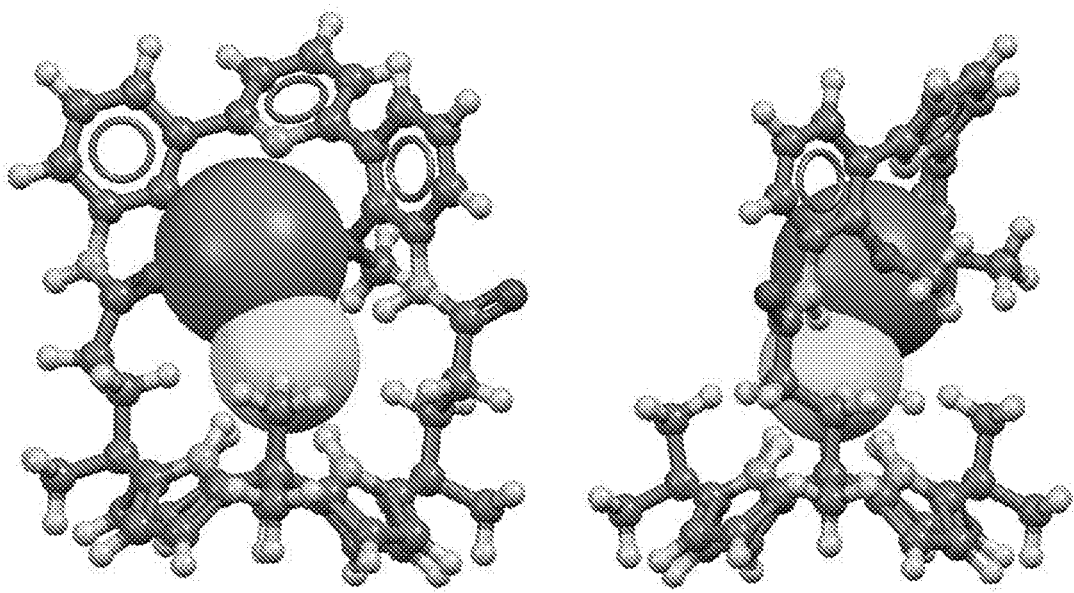
FIG. 15 shows front (left) and side (right) views of the DFT optimized structure of the NaCl complex of receptor 2.
Figure 16:
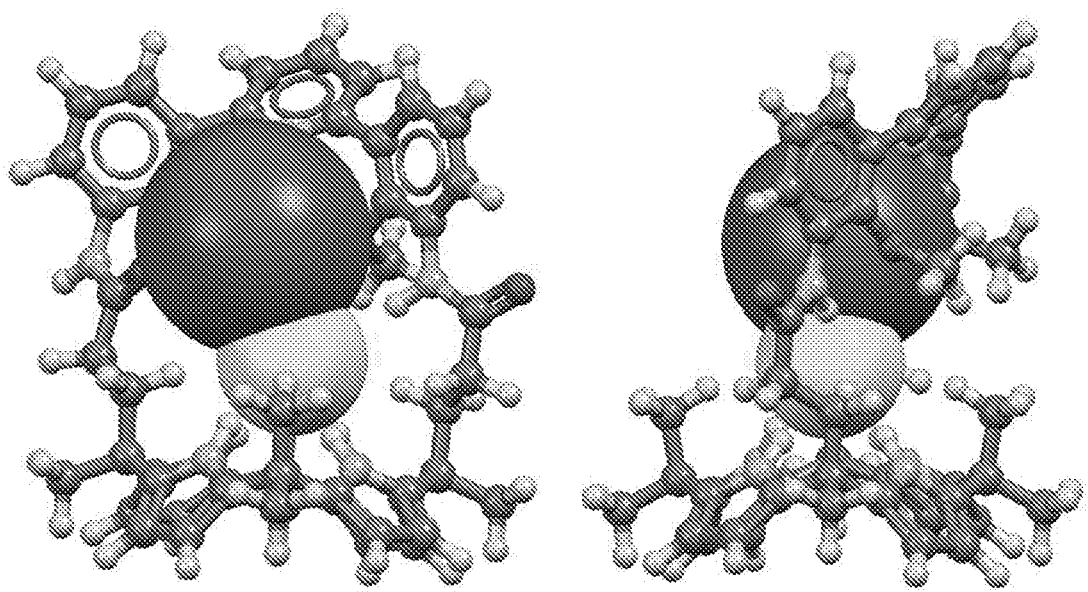
FIG. 16 shows front (left) and side (right) views of the DFT optimized structure of the KCl complex of receptor 2.
Figure 17:
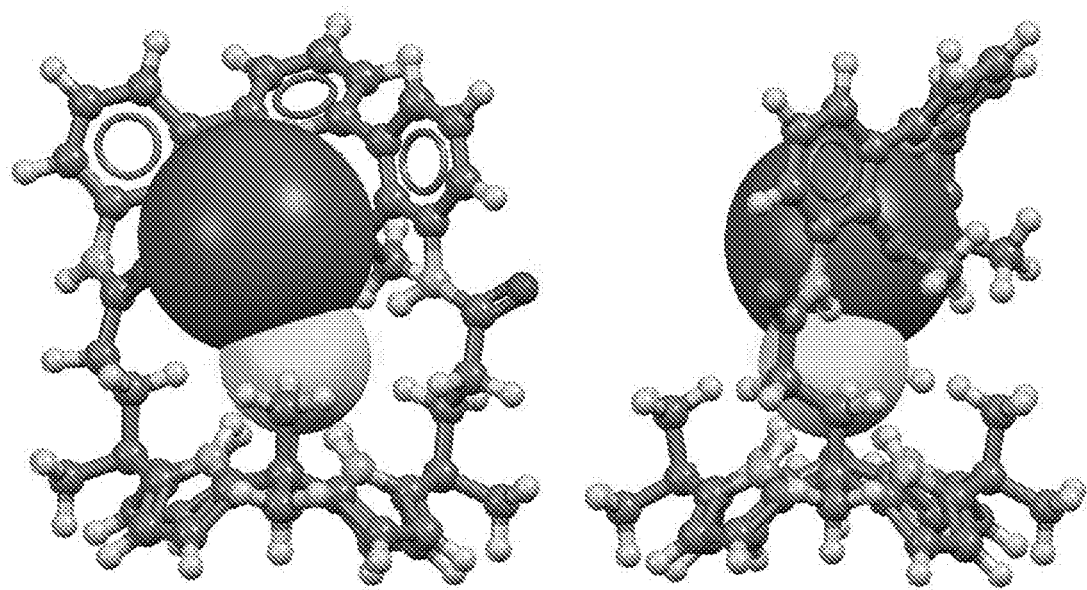
FIG. 17 shows front (left) and side (right) views of the DFT optimized structure of the CsCl complex of receptor 2.
Figure 18:
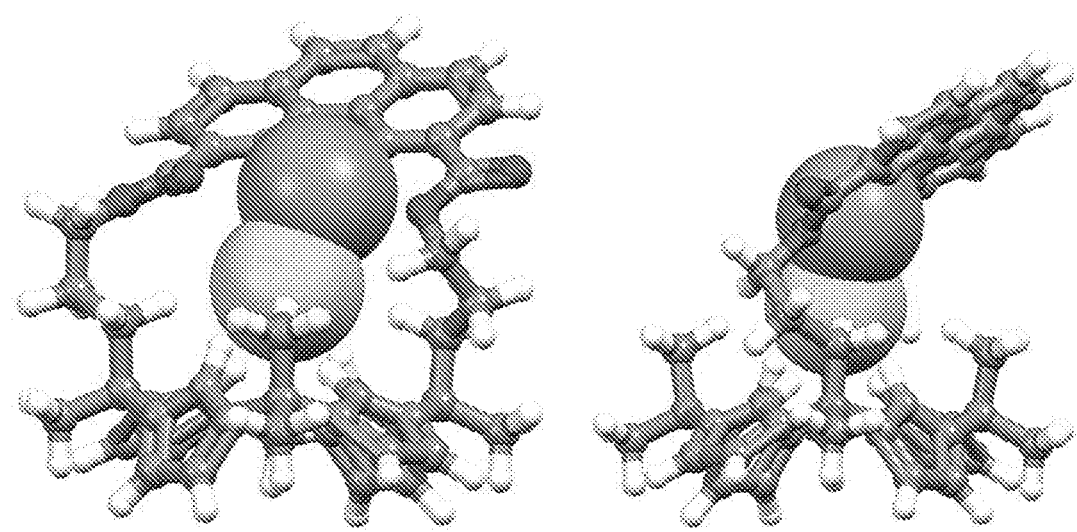
FIG. 18 shows front (left) and side (right) views of the DFT optimized structure of the LiCl complex of receptor 3.
Figure 19:
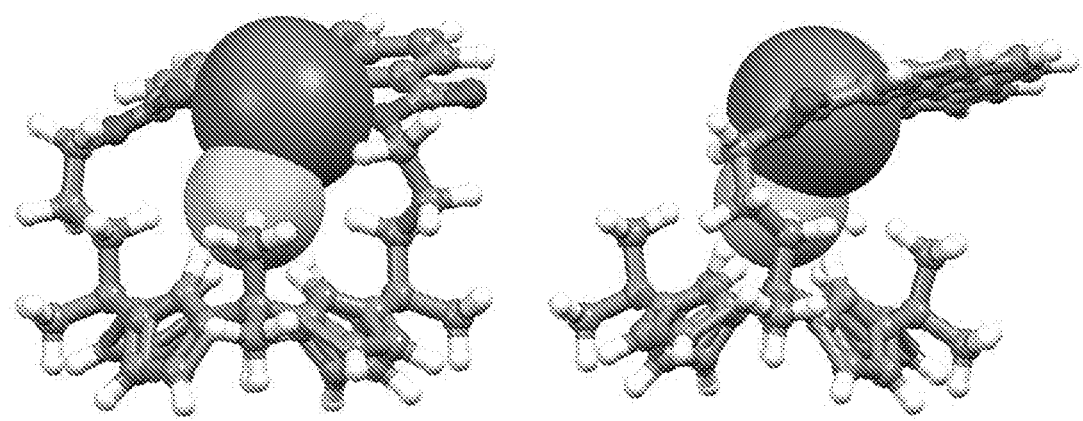
FIG. 19 shows front (left) and side (right) views of the DFT optimized structure of the NaCl complex of receptor 3.
Figure 20:
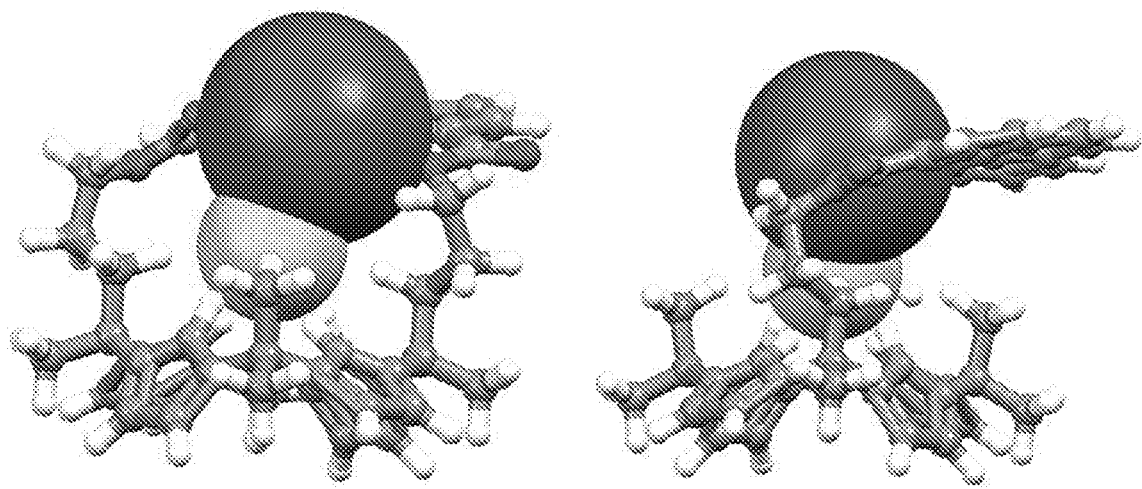
FIG. 20 shows front (left) and side (right) views of the DFT optimized structure of the KCl complex of receptor 3.
Figure 21:
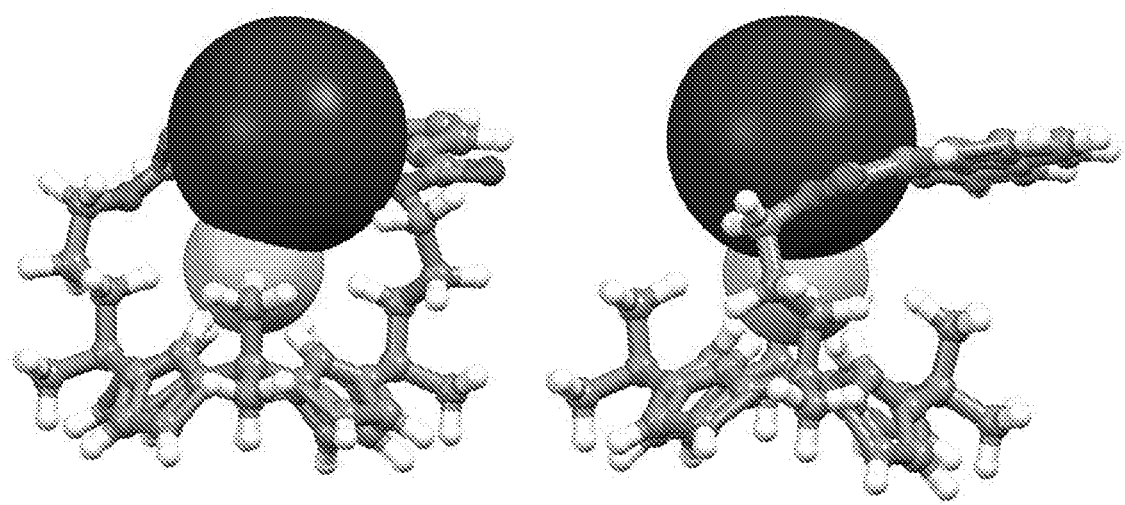
FIG. 21 shows front (left) and side (right) views of the DFT optimized structure of the CsCl complex of receptor 3.
Figure 22:
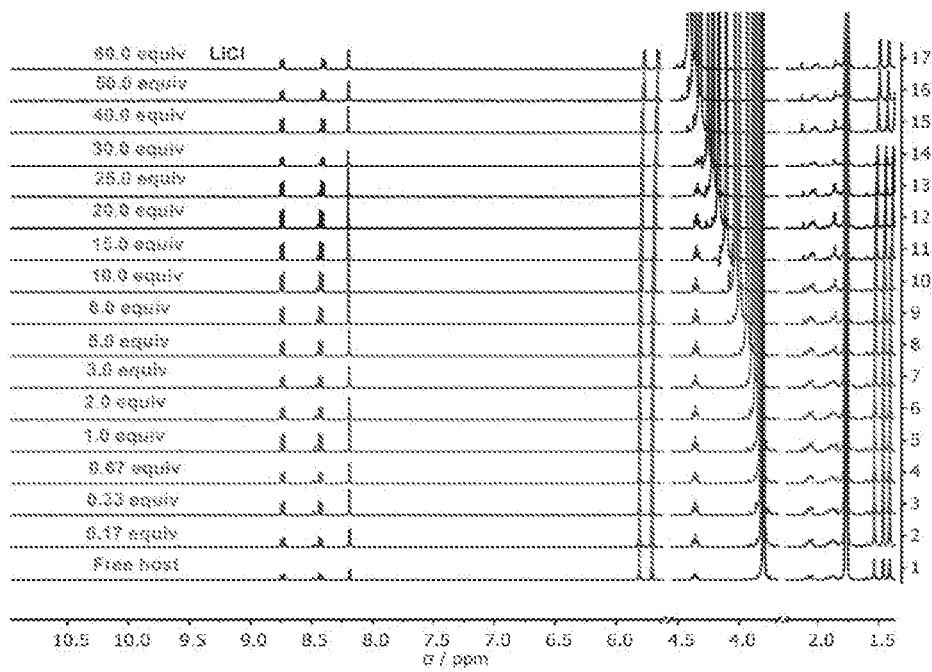
FIG. 22 shows an ¹H NMR spectroscopic titration of receptor 3 with LiCl in a mixed solvent consisting of THF-d₈/D₂O (9/1, v/v). The concentration of 3 was 3.0 mM.
Figure 23:
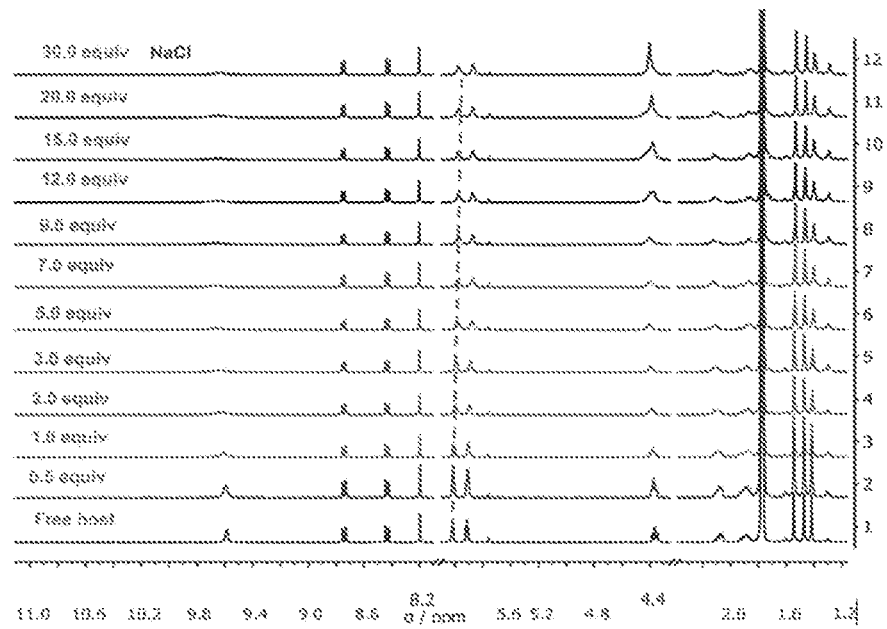
FIG. 23 shows an ¹H NMR spectroscopic titration of receptor 3 with NaCl in a mixed solvent consisting of THF-d₈/D₂O (9/1, v/v). The concentration of 3 was 3.0 mM.
Figure 24:
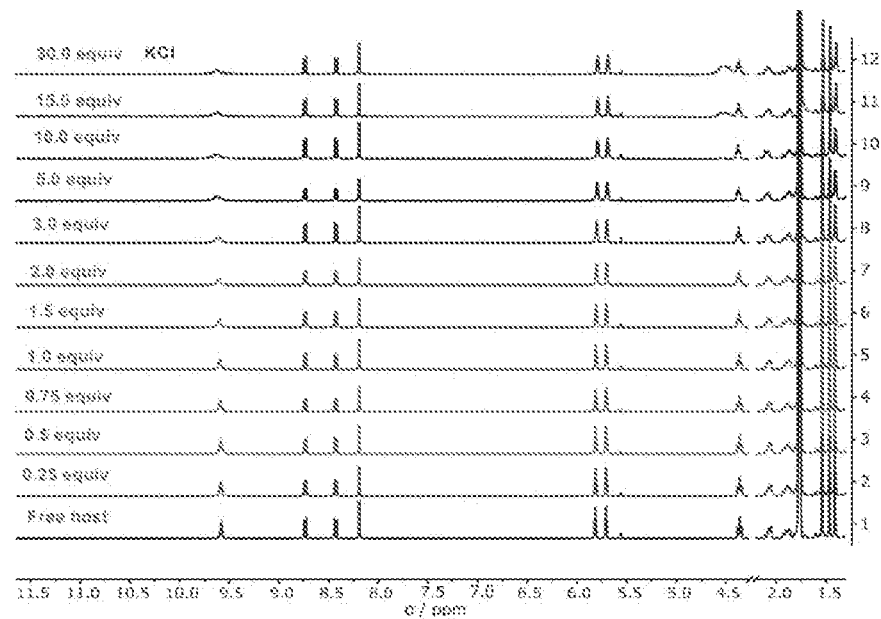
FIG. 24 shows an ¹H NMR spectroscopic titration of receptor 3 with KCl in a mixed solvent consisting of THF-d₈/D₂O (9/1, v/v). The concentration of 3 was 3.0 mM.
Figure 25:
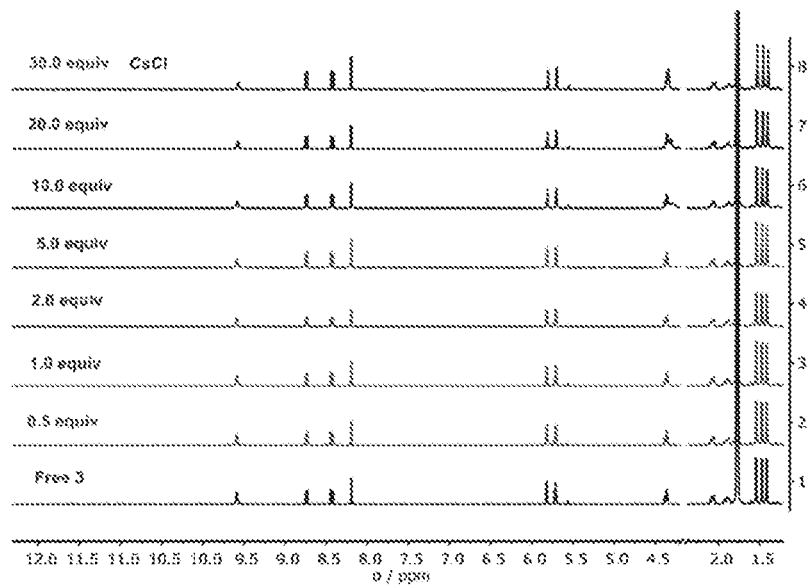
FIG. 25 shows an ¹H NMR spectroscopic titration of receptor 3 with CsCl in a mixed solvent consisting of THF-d₈/D₂O (9/1, v/v). The concentration of 3 was 3.0 mM.

Further support for the fact that 2 and 3 are capable of capturing LiCl came from single crystal Xray diffraction analyses. Suitable crystals of the LiCl complexes of 2 (2·LiCl) and 3 (3·LiCl) were obtained by subjecting a $CH_2Cl_2/CH_3OH/CH_3CN$ solution of 2 or a $CH_3CN/CH_3OH$ solution of receptor 3 to slow evaporation in the presence of excess LiCl, respectively. In contrast to what was seen in the case of 1. LiCl, where a water molecule was observed to bridge the Li$^+$ cation and the Cl$^-$ anion (He et al., 2016) receptors 2 and 3, as anticipated, entrap the LiCl ion pair directly within their cavities. This gives rise to close Li$^+$ . . . Cl$^-$ distances of 2.67 Å and 2.38 Å, respectively (FIGS. 4A & 4B). In the case of 2·LiCl, both the Li$^+$ and Cl$^-$ ions were found entirely embedded within the cavity of receptor 2, while in the case of 3·LiCl, the cation was forced to extrude from the cavity leading to distortion of the receptor framework. The solid-state structures of 2·NaCl, 2·KCl, and 2·CsCl were also obtained (FIGS. 5A-5D). Although the Na$^+$, K$^+$, and Cs$^+$ are all complexed by the hemispherand portion of receptor 2, as the ionic radius increases from Li$^+$ to Cs$^+$, the cations extrude further and further from the receptor cavity. Such findings suggested that both 2 and 3 might prove selective for LiCl over other alkaline metal chloride salts. Since 3 possesses the smallest cavity within the series 1-3 it was imagined that it might prove to be an even more effective extractant than 2.

Figure 26:
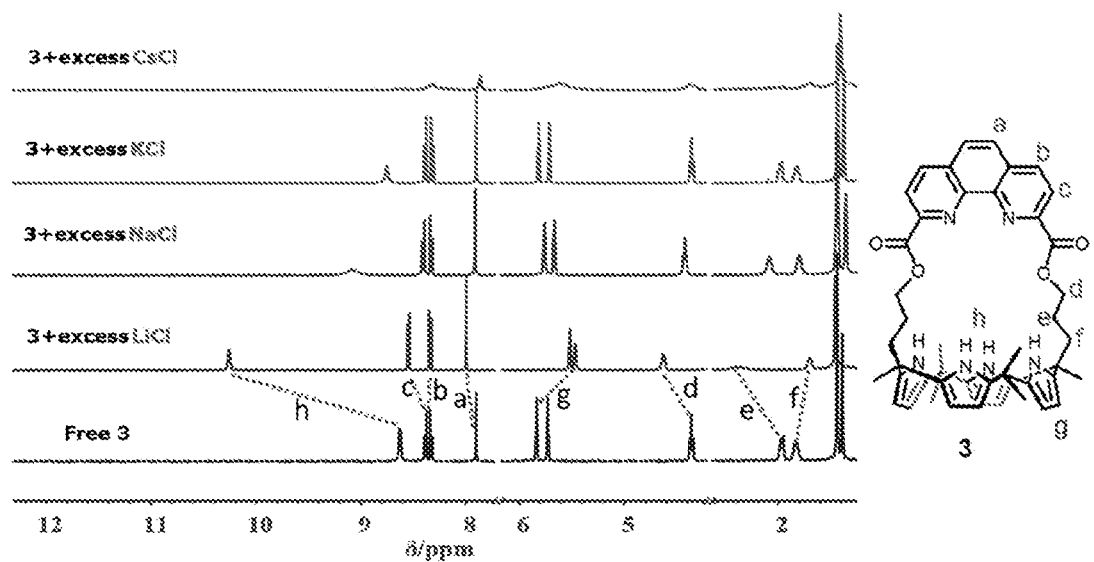
FIG. 26 shows partial ¹H NMR spectra of a 4.0 mM solution of free 3 recorded in the absence and presence of excess LiCl, NaCl, KCl, or CsCl in CDCl₃/CD₃OD (9/1, v/v). All spectra were recorded after allowing the solid phase and the organic phase to equilibrate for 24 h.

To obtain more direct experimental insights into the binding selectivities of 2, $^1$H NMR spectroscopic titrations were performed in THF-$d_8$/$D_2O$ (9:1, v/v) (FIGS. 6-13). The resulting data could be fit to a 1:1 binding model giving calculated affinity constants of $(8.3\pm0.3)\times10^2$ M$^{-1}$, $(1.2\pm0.3)\times b\ 10^4$ M$^{-1}$, $(6.7\pm2.5)\times10^3$ M$^{-1}$, and $(2.5\pm0.6)\times10^3$ M$^{-1}$ for LiCl, NaCl, KCl and CsCl, respectively. This resulting binding selectivity, namely NaCl>KCl>CsCl>LiCl, differs from what was inferred from the gas phase DFT calculations (LiCl>NaCl>KCl>CsCl) (FIGS. 14-21, Tables 1-3). The strong reduction in the relatively LiCl affinity is ascribed to the presence of water in the solvent mixture and the particularly "hard" nature of the lithium cation ($\Delta G_{hyd}$=-475 kJ·mol$^{-1}$ for Li$^+$ vs. $\Delta H_{hyd}$=365 kJ·mol$^{-1}$, -295 kJ·mol$^{-1}$, and -250 kJ·mol$^{-1}$ for Na$^+$, K$^+$, and Cs$^+$, respectively, Marcus, 1991). When 3 was subject to analogous titrations, no appreciable changes in any of the proton signals for 3 were observed after 30 equivalents of MCl (M=Li, Na, K, Cs) were added (FIGS. 22-25). This latter finding is rationalized in terms of the interactions between 3 and these alkali metal salts being insufficient to compete effectively with hydration in this mixed aqueous medium. However, the treatment of receptor 3 in a water-free mixture of CDCl$_3$/CD$_3$OD (9:1, v/v) with excess LiCl to leads to chemical shift changes consistent with the concurrent complexation of both the Li$^+$ and Cl$^-$. No appreciable changes in any of the receptor-based proton signals were seen when receptor 3 was treated with excess NaCl, KCl, or CsCl (FIG. 26).

TABLE 1

Comparison of the selected distances (Å) from the single-crystal structures (crysl) and their DFT calculated structures (calcd).

| | | Complexes | | | |
|---|---|---|---|---|---|
| | | 2 LiCl | 2 NaCl | 2 KCl | 2 CsCl |
| $d_{M-Cl}{}^a$ | crystl | 2.667 | 2.911 | 3.153 | 3.400 |
| | calcd | 2.425 | 2.686 | 2.985 | 3.397 |
| $d_{N-Cl}{}^b$ | crystl | 3.379 | 3.352 | 3.298 | 3.277 |
| | calcd | 3.593 | 3.459 | 3.420 | 3.388 |
| $d_{N-M}{}^c$ | crystl | 2.312 | 2.734 | 3.075 | 3.271 |
| | calcd | 2.336 | 2.886 | 2.973 | 3.363 |
| $d_{O-M}{}^d$ | crystl | 1.969 | 2.333 | 2.784 | 3.120 |
| | calcd | 1.939 | 2.344 | 2.716 | 3.250 |

$^a$The distances between the alkali metal cations and chloride.
$^b$The averaged distances between the pyrrole N and chloride.
$^c$The distances between the pyridine N and alkali metal cations.
$^d$The averaged distances between the alkali metal cations and the methoxy O.

TABLE 2

Calculated Gas-Phase Binding Energy ($E_{BSSE}$) for Four Ion Pair Complexes of 2.

| | Complexes | | | |
|---|---|---|---|---|
| | 2•LiCl | 2•NaCl | 2•KCl | 2•CsCl |
| $E_{BSSE}$/(kcal/mol): | -221.63 | -204.51 | -179.86 | -156.78 |

TABLE 3

Calculated Gas-Phase Binding Energy ($E_{BSSE}$) for Four Ion Pair Complexes of 3.

| | Complexes | | | |
|---|---|---|---|---|
| | 3•LiCl | 3•NaCl | 3•KCl | 3•CsCl |
| $E_{BSSE}$/(kcal/mol): | -213.91 | -193.53 | -168.73 | -145.24 |

Figure 27:
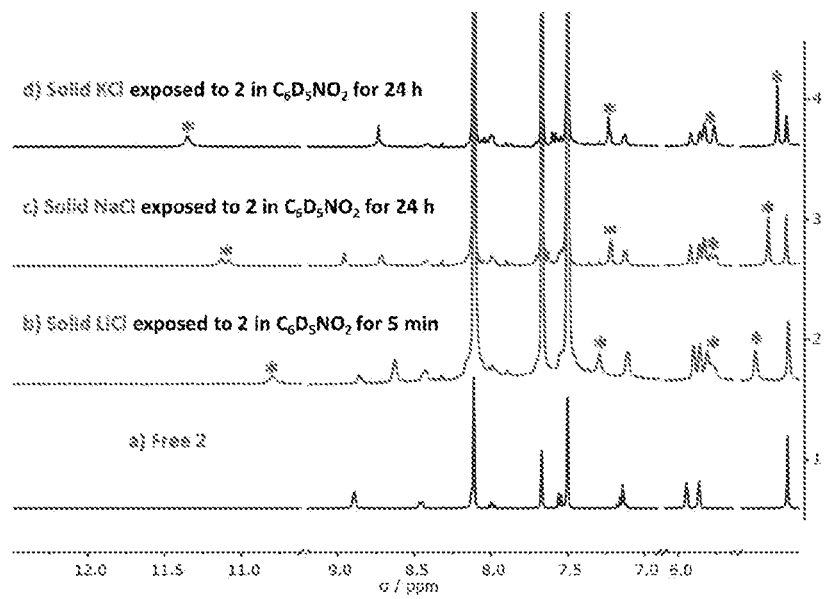
FIG. 27 shows partial ¹H NMR spectra of (a) free receptor 2 (4.0 mM) in C₆D₅NO₂; (b) receptor 2 (4 mM in C₆D₅NO₂) contacted with excess solid LiCl for 5 min; (c) receptor 2 (4 mM in C₆D₅NO₂) contacted with excess solid NaCl for 24 h; (d) receptor 2 (4 mM in C₆D₅NO₂) contacted excess solid KCl for 24 h. Two sets of peaks were observed, indicating the slow exchange between the receptor 2 and the complexes.
Figure 28:
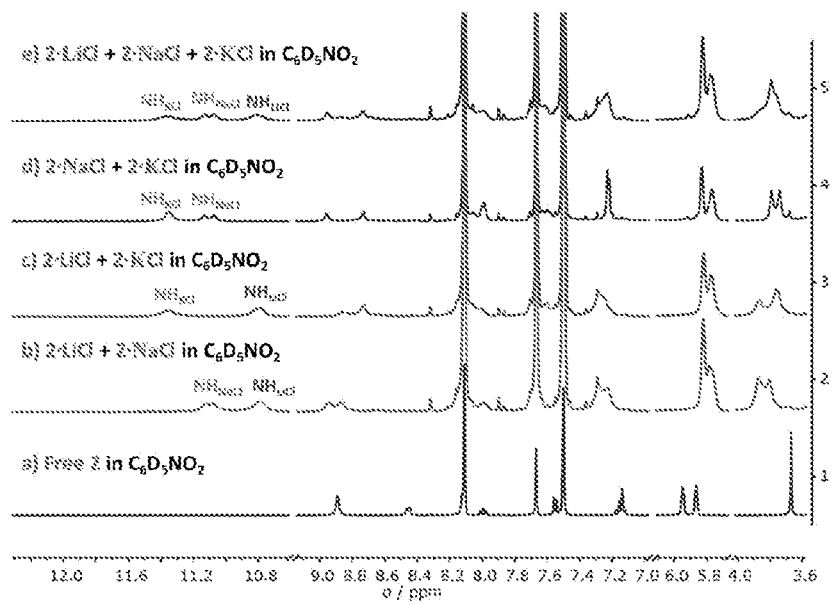
FIG. 28 shows partial ¹H NMR spectra of (a) free receptor 2 (4.0 mM) in C₆D₅NO₂; (b) complex 2·LiCl (4 mM) in C₆D₅NO₂+complex 2·NaCl (4 mM) in C₆D₅NO₂ (1:1, v/v); (c) complex 2·LiCl (4 mM) in C₆D₅NO₂+complex 2·KCl (4 mM) in C₆D₅NO₂ (1:1, v/v); (d) complex 2·NaCl (4 mM) in C₆D₅NO₂+complex 2·KCl (4 mM) in C₆D₅NO₂ (1:1, v/v); (e) complex 2·LiCl (4 mM) in C₆D₅NO₂+complex 2·NaCl (4 mM) in C₆D₅NO₂+complex 2·KCl (4 mM) in C₆D₅NO₂ (1:1:1, v/v/v).
Figure 29:
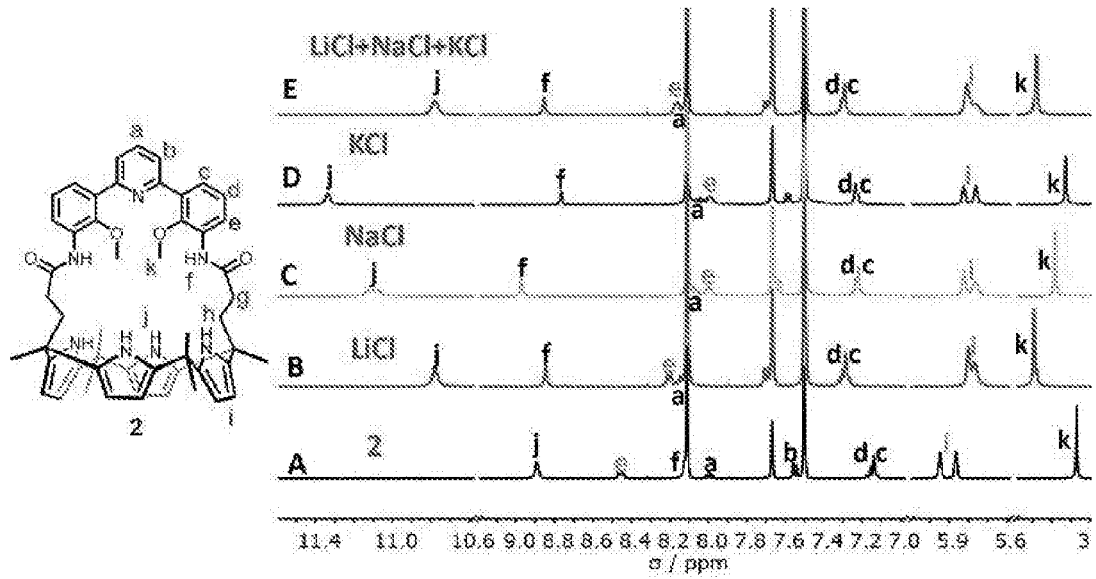
FIG. 29 shows partial ¹H NMR spectra of a 4.0 mM solution of (A) 2 only; (B) 2+excess solid LiCl; (C) 2+excess solid NaCl; (D) 2+excess solid KCl; and (E) 2+100 equiv LiCl+100 equiv NaCl+100 equiv KCl in C₆D₅NO₂.
Figure 30:
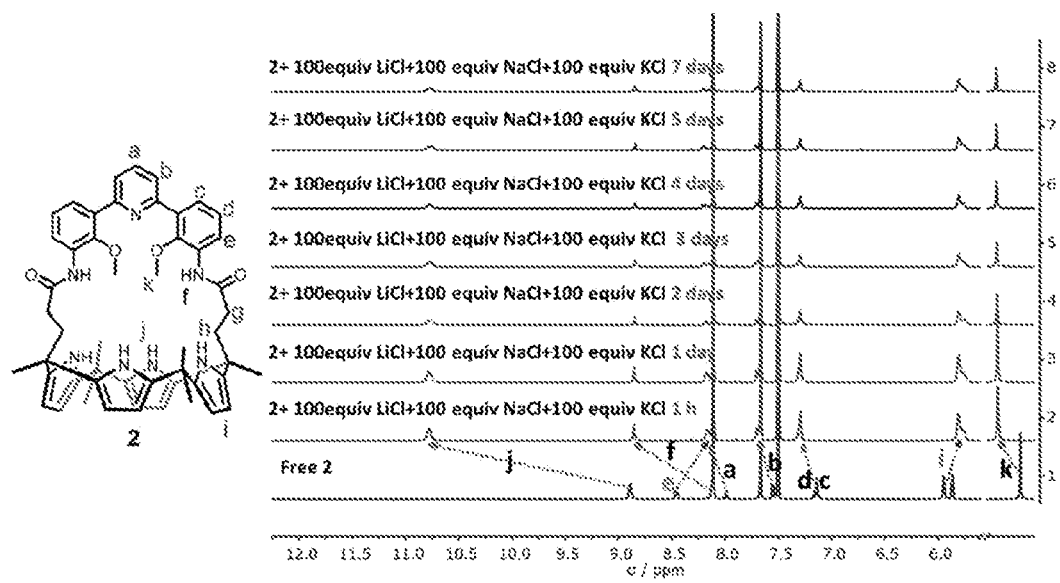
FIG. 30 shows partial ¹H NMR spectra of receptor 2 (4.0 mM in C₆D₅NO₂) recorded in the absence and presence of 100 equiv of equal molar quantities of LiCl, NaCl and KCl after letting stand for 1 h, 1 day, 2 days, 3 days, 4 days, 5 days, and 7 days, respectively. No more change in the proton signals is seen over time once receptor 2 was fully saturated with LiCl, something that occurs within 1 h.
Figure 31:
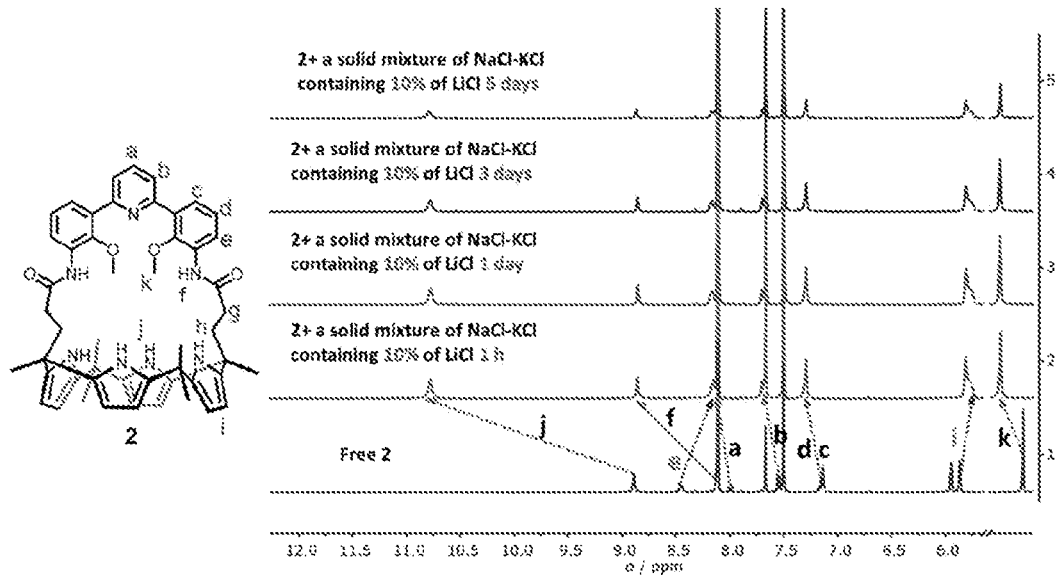
FIG. 31 shows partial ¹H NMR spectra of receptor 2 (4.0 mM in C₆D₅NO₂) recorded in the absence and presence of an equal-by-mass solid mixture of NaCl and KCl containing 10% (mass content) of LiCl and allowing to stand for 1 h, 1 day, 3 days, and 5 days, respectively. No change in the proton signals as a function of time is seen once receptor 2 is fully saturated with LiCl, something which occurs within 1 h.
Figure 32:
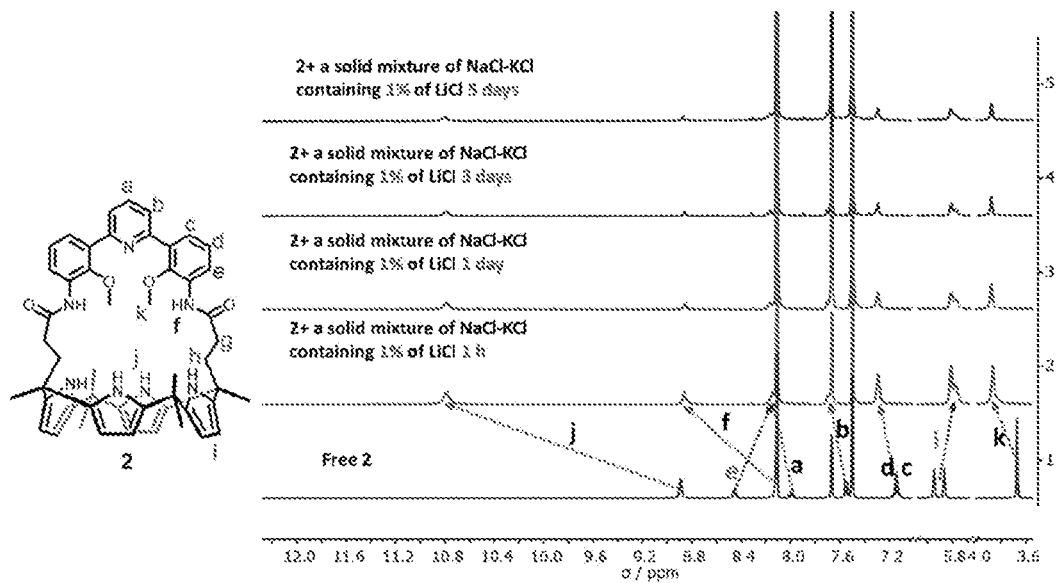
FIG. 32 shows partial ¹H NMR spectra of receptor 2 (4.0 mM in C₆D₅NO₂) recorded in the absence and presence of an equal-by-mass solid mixture of NaCl and KCl containing 1% (mass content) of LiCl and allowing to stand for 1 h, 1 day, 3 days, and 5 days, respectively. No changes in the proton signals occur as a function of time once receptor 2 is fully saturated by LiCl, something that occurs within 1 h.

The above findings elicited the idea that 2 and 3 might prove effective as extractants for LiCl under both SLE and LLE conditions in the presence of excess NaCl and KCl, as would be present in common lithium-containing salt flats. In a first study, solutions of 2 in $C_6D_5NO_2$ were layered over solid samples consisting of excess powdered LiCl, NaCl, and KCl, respectively. Control experiments revealed that exchange between the different receptor/salt complexes is slow on the NMR time scale (FIGS. 27 & 28). Thus, each extracted complex (i.e., 2·LiCl, 2·NaCl, and 2·KCl) in the organic phase could be recognized directly by $^1$H NMR spectroscopy and the relative concentrations of the free and bound forms of the receptor measured by integrating the respective signals. On this basis, it was found that receptor 2 was capable of extracting efficiently LiCl, NaCl and KCl into nitrobenzene over the course of 48 h (FIG. 29). After this equilibration time, receptor 2 was almost 100% loaded in the case of each salt. As inferred from $^1$H NMR spectral studies, high selectivity (~100%) was seen for LiCl over NaCl and KCl in the case of a competitive solid/liquid salt extraction study wherein a solution of 2 in $C_6D_5NO_2$ was layered over a mixture of LiCl, NaCl and KCl (100:100:100, molar ratio relative to 2) and allowed to stand for 1 h. Little change in the $^1$H NMR spectrum is seen over time (up to 7 days), indicating that the selectivity for LiCl under these conditions of receptor saturation is likely thermodynamic in origin (FIG. 30). Additionally, 2 was found capable of selectively extracting LiCl from mixtures of salts (NaCl and KCl; 1:1, m/m) containing either 10% or only 1% of LiCl by mass (FIGS. 31 & 32).

Figures 33A, 33B, 33C, 33D, 33E, 33F:
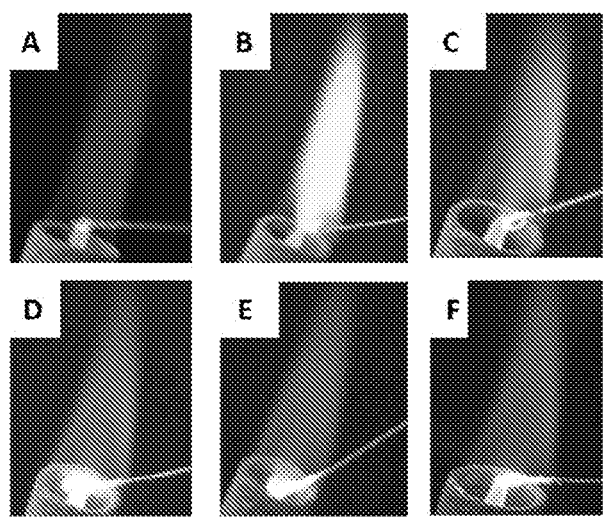
FIGS. 33A-33F show flame test experiments involving control aqueous solutions consisting of (FIG. 33A) LiCl.
Figures 34A, 34B:
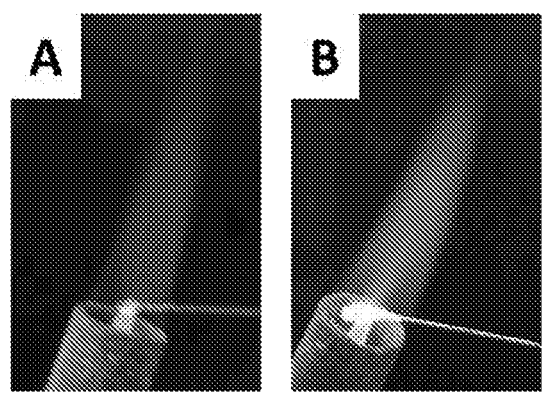
FIGS. 34A & 34B show images of flame experiments involving (FIG. 34A) LiCl.

Further support for the fact that receptor 2 can act as an ion-pair extractant for LiCl with selectivity towards LiCl over NaCl and KCl came from the qualitative flame tests. Control experiments confirmed the expected colors, namely red, yellow and purple (FIGS. 33A-33C) when a loop was dipped into 1 M aqueous Further support for the fact that receptor 2 can act as an ion-pair extractant for LiCl with selectivity towards LiCl over NaCl and KCl came from the qualitative flame tests. Control experiments confirmed the expected colors, namely red, yellow and purple (FIGS. 33A-33C) when a loop was dipped into 1 M aqueous solutions of LiCl, NaCl, and KCl, respectively, and held within a flame. The red flame characteristic of lithium was seen when clean loops were dipped into solutions of 2 in nitrobenzene after treatment with a mixture of LiCl, NaCl and KCl (in a 100:100:100, molar ratio) (FIGS. 34A & 34B). Similar color features of lithium were also seen when mixtures of NaCl and KCl containing either 10% or 1% LiCl (by mass) were subject to the same qualitative analysis (FIGS. 33D & 33E).

Figure 35:
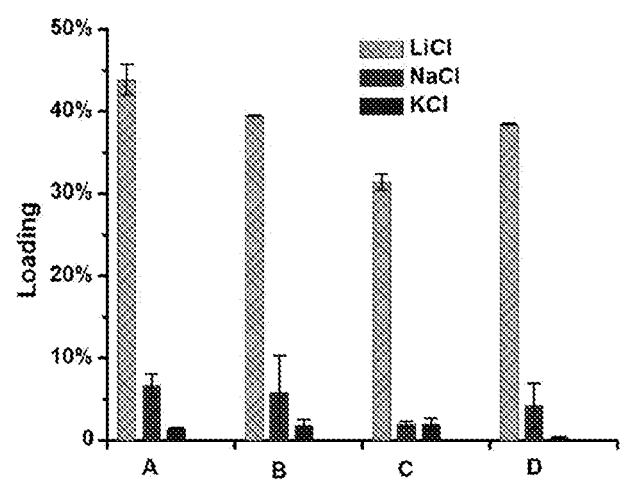
FIG. 35 shows the results of ICP-MS analyses showing the percent receptor loading of the indicated alkaline chloride salt after extraction from solid mixtures of (A) LiCl, NaCl and KCl (100:100:100, molar ratio), (B) NaCl and KCl containing 10% of LiCl (mass content), and C) analogous experiments where the LiCl content was 1% by mass, the concentration of receptor 2 was 4 mM in nitrobenzene in all three studies. (D) Analogous studies involving a solid mixture of NaCl and KCl containing 200 ppm of LiCl (by mass) using receptor 3 (3 mM in chloroform).

More quantitative support for the suggestion that 2 is selective for LiCl came from inductively coupled mass spectrometric (ICP-MS) analyses. These experiments were performed by layering nitrobenzene solutions of 2 over the above-mentioned salt mixtures for 48 h. In each case, the organic phase was then separated off and back extracted with 0.2 M sulfuric acid. The resulting aqueous phase was then diluted with 2% aqueous $HNO_3$ and subject to ICP-MS analysis. After accounting for uptake of salts by the solvent alone, the loading of each ion pair was calculated and reported in terms of the percentage of total receptor sites bound (FIG. 35, Tables 4 & 5).

TABLE 4

Summary of ICP-MS Results Involving Solid-liquid Extractions.

| Extractants | Mixture salts | Extracted salts | Observed by ICP-MS/ppb | Receptor bound (loading)/% |
|---|---|---|---|---|
| 2 (4 mM) | LiCl, NaCl, KCl 100× molar excess each relative to 2 | LiCl NaCl KCl | 345 134 42 | 62 ± 8.8 7 ± 6.6 1 ± 0.4 |
| 2 (4 mM) | NaCl, KCl (1:1, m/m), containing 10% of LiCl | LiCl NaCl KCl | 311 17 38 | 55 ± 2.1 1 ± 0.3 1 ± 0.3 |
| 2 (4 mM) | NaCl, KCl (1:1, m/m) containing 1% of LiCl | LiCl NaCl KCl | 254 130 73 | 40 ± 0.3 7 ± 1.4 2.0 ± 0.7 |
| 3 (3 mM) | NaCl, KCl (1:1, m/m) containing 200 ppm of LiCl | LiCl NaCl KCl | 160 53 1 | 38 ± 0.5 4.2 ± 2.7 0 ± 0.1 |

Note:
Reported concentrations are after dilution with a known amount of aqueous 2% nitric acid. The error values given represent the deviations seen in duplicate measurements. The term receptor bound refers to the percentage of the total possible receptor sites populated with alkali metal ions. The values recorded for the bound receptor percentage were calculated by accounting for the lithium, sodium and potassium levels found in the blank controls.

TABLE 5

Results from an ICP-MS analysis for confirming the selective solid-liquid extraction.

| Extractants | Mixture salts | Extracted salts | SLE with receptors/ppb | SLE without receptors/ppb |
|---|---|---|---|---|
| 2 (4 mM) | LiCl, NaCl, KCl 100× molar excess each relative to 2 | LiCl NaCl KCl | 350.5 1011.8 92.7 | 0.5 877.4 50.3 |
| 2 (4 mM) | NaCl, KCl (1:1, m/m), containing 10% of LiCl | LiCl NaCl KCl | 311.4 863.2 99.3 | 0.5 879.9 61.0 |
| 2 (4 mM) | NaCl, KCl (1:1, m/m) containing 1% of LiCl | LiCl NaCl KCl | 254.2 1236.0 155.5 | 0.5 1106.0 82.2 |
| 3 (3 mM) | NaCl, KCl (1:1, m/m) containing 200% of LiCl | LiCl NaCl KCl | 160.3 522.0 19.5 | 0.3 469.3 19.7 |

Note:
Reported concentrations are averaged results in duplication measurements after dilution with a known amount of aqueous 2% nitric acid and were achieved by subtracting the lithium, sodium and potassium levels found in the blank controls.

In the case of the mixture consisting of LiCl, NaCl and KCl in a 100:100:100 molar ratio, the loading of LiCl was estimated to be ca. 62%, while in the case of the solid-liquid extraction experiments involving lower relative LiCl concentrations (i.e., 10% and 1% by mass), the loading levels were estimated to be ca. 55% and 45%, respectively. In contrast, the loading of NaCl and KCl was found to be <7% and <2%, respectively. This was found to be true for all three LiCl ratios. It is noted that the absolute loading levels inferred from the ICP-MS studies are lower than the 100% loading levels calculated from the $^1H$ NMR spectroscopic studies, even if the selectivity ratios were similar. The relatively low total loading levels seen in the ICP-MS studies may be accounted for by continual dilution before the final elemental analysis.

Figure 36:
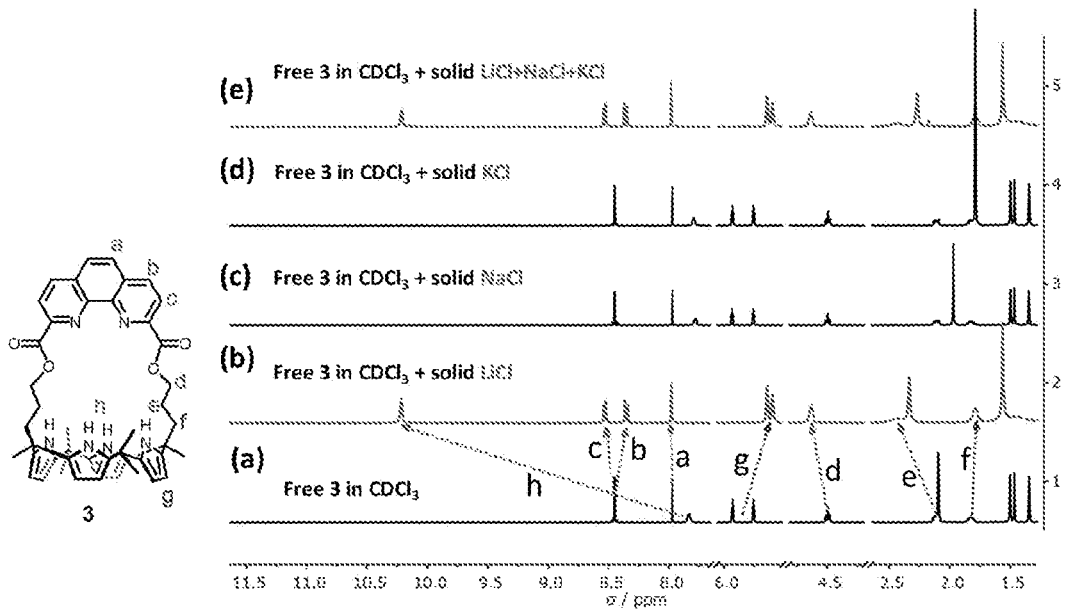
FIG. 36 shows partial $^1$H NMR spectra of a 3.0 mM solution (CDCl$_3$) of (a) 3 only and 3 with (b) excess LiCl, (c) excess NaCl, (d) excess KCl, (e) excess LiCl+NaCl+KCl. All spectra were recorded after sonicating for 1 h.
Figure 37:
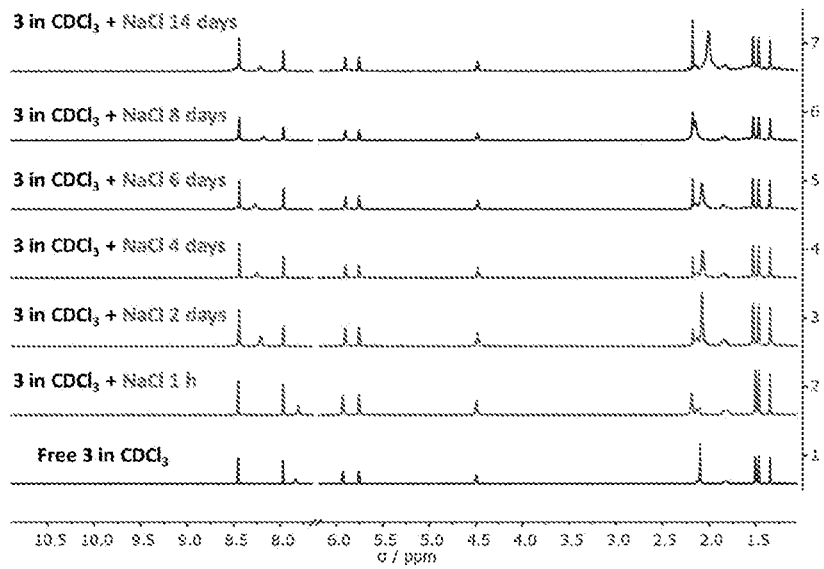
FIG. 37 shows partial $^1$H NMR spectra of receptor 3 (3.0 mM in CDCl$_3$) recorded in the absence and presence of excess solid NaCl after allowing to stand for 1 h, 2 days, 4 days, 6 days, 8 days, and 14 days, respectively. No evidence of NaCl extraction was seen within 14 days.
Figure 38:
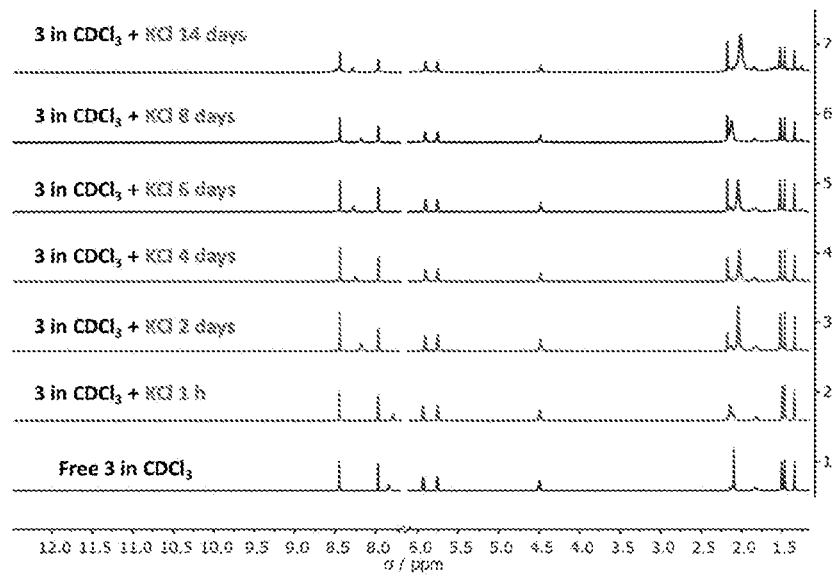
FIG. 38 shows partial $^1$H NMR spectra of receptor 3 (3.0 mM in CDCl$_3$) recorded in the absence and presence of excess solid KCl after allowing to stand for 1 h, 2 days, 4 days, 6 days, 8 days, and 14 days, respectively. No evidence of KCl extraction was observed within 14 days.

Much to our surprise, receptor 3 proved even more selective for LiCl relative to NaCl and KCl than 2 when tested as an extractant under conditions of SLE. After a 3.0 mM solution of 3 in $CDCl_3$ was allowed to stand over excess quantities of solid LiCl, NaCl and KCl, respectively, a new set of signals corresponding to the complex 3·LiCl was observed in the sample involving solid LiCl (FIG. 36). In contrast, no appreciable change in the proton signals of 3 was seen after contacting with solid NaCl or KCl, even if the putative equilibration time was extended to two weeks (FIGS. 37 & 38). Such observations are taken as an indication that receptor 3 acts as a selective extractant for LiCl under SLE conditions where chloroform serves as the organic phase.

Figure 39:
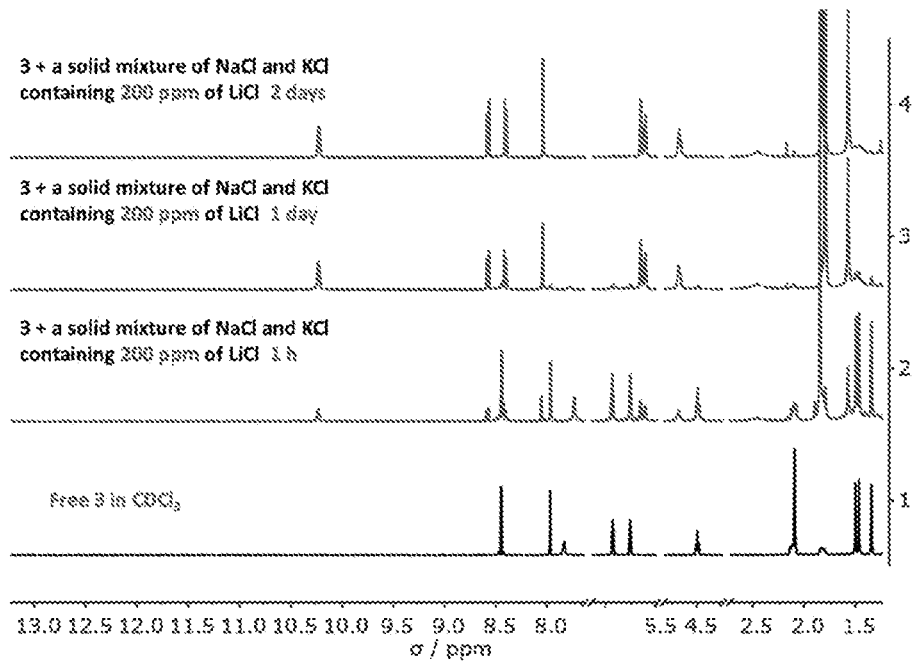
FIG. 39 shows partial $^1$H NMR spectra of receptor 3 (3.0 mM in CDCl$_3$) recorded in the absence and presence of an equal-by-mass solid mixture of NaCl and KCl containing 200 ppm (by weight) of LiCl and allowing to stand for 1 h, 1 day, and 2 days, respectively.

To test this concept further, receptor 3 was tested as an extractant in SLE studies involving solid samples with extremely high Na(K)/Li ratios. Specifically, a solution of 3 in $CDCl_3$ was layered over a solid NaCl—KCl (1:1, by mass) mixture containing 200 ppm LiCl and subject to sonication for 1 h. A new set of peaks was seen in the $^1H$ NMR spectrum that was readily assigned to 3. LiCl, along with signals corresponding to free 3. Expanding the exposure time to 48 h led to essentially complete conversion to the complex form (FIG. 39). Even under these long contact times, no new peaks corresponding to either 3. NaCl or 3. KCl were observed. The fact that, under this extreme condition, LiCl was selectively extracted to the chloroform phase was qualitatively supported by flame test experiments (FIG. 33F) and quantitative ICP-MS studies analogous to those described above (FIG. 35D, Tables 4 & 5). In the case of the latter one, the loading of LiCl was estimated to be ca. 38%, while that of NaCl and KCl were too low to be assessed with confidence in light of the relatively high background levels. This may be the first example of an ion pair receptor to complex effectively small quantities of LiCl under SLE conditions in the presence of large quantities of NaCl and KCl, two common salts that are likely to be in excess under possible real-world application scenarios.

Figure 40:
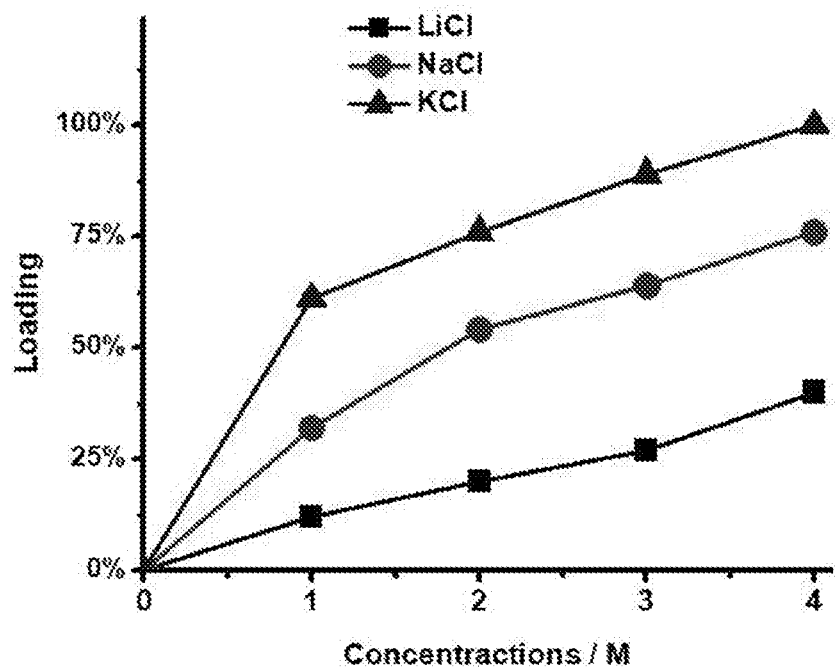
FIG. 40 shows liquid-liquid extraction of LiCl (squares), NaCl (circles), and KCl (triangles). The loading is defined as the molar percentage of extractant containing MCl (where M=Li, Na, K) after exposure to the aqueous MCl solution. The concentration of 2 in C$_6$D$_5$NO$_2$ is 4.0 mM.
Figure 41:
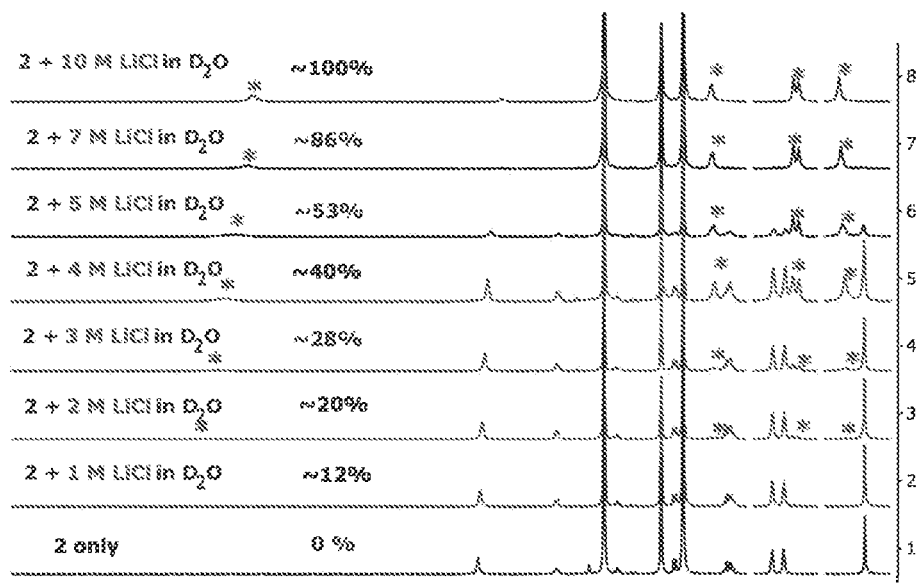
FIG. 41 shows partial $^1$H NMR spectra of a 4.0 mM solution of 2 in C$_6$C$_5$NO$_2$ recorded after exposure to D$_2$O and 1 M, 2 M, 3 M, 4 M, 5 M, 7 M, and 10 M of LiCl in D$_2$O, where the extraction efficiencies are estimated to be 0%, 12%, 20%, 28%, 40%, 53%, 86%, and 100%, respectively.
Figure 42:
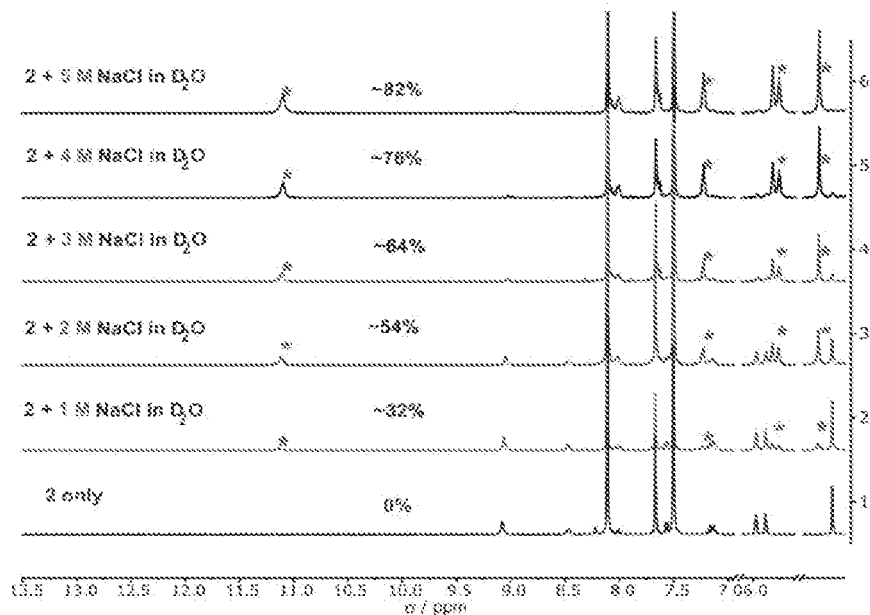
FIG. 42 shows partial $^1$H NMR spectra of a 4.0 mM solution of 2 in C$_6$C$_5$NO$_2$ recorded after exposure to D$_2$O and 1 M, 2 M, 3 M, 4 M, and 5 M of NaCl in D$_2$O, where the extraction efficiencies are estimated to be 0%, 32%, 54%, 64%, 76%, and 82%, respectively.
Figure 43:
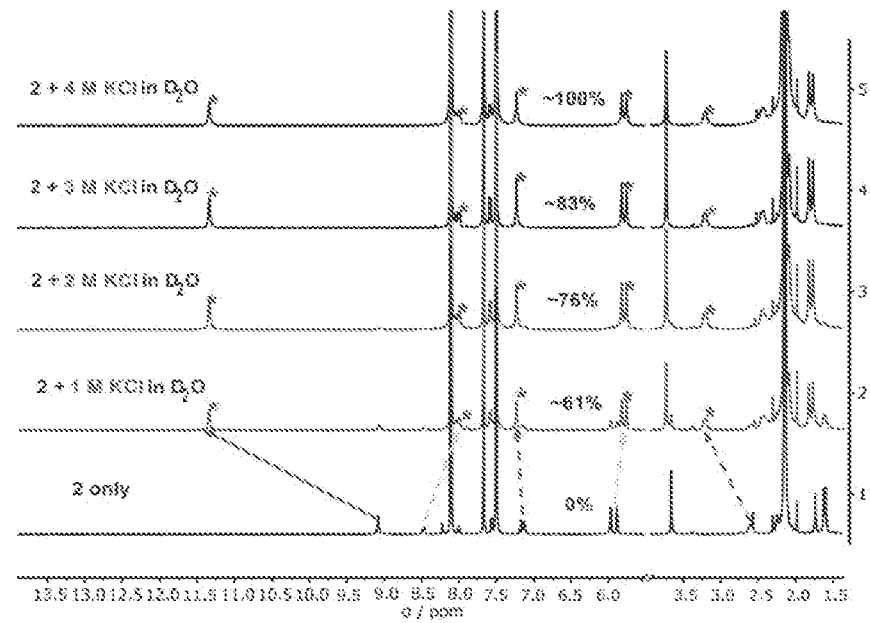
FIG. 43 shows partial $^1$H NMR spectra of a 4.0 mM solution of 2 in C$_6$C$_5$NO$_2$ recorded after exposure to D$_2$O and 1 M, 2 M, 3 M, and 4 M of KCl in D$_2$O, where the extraction efficiencies are estimated to be 0%, 61%, 76%, 83%, and 100%, respectively.
Figure 44:
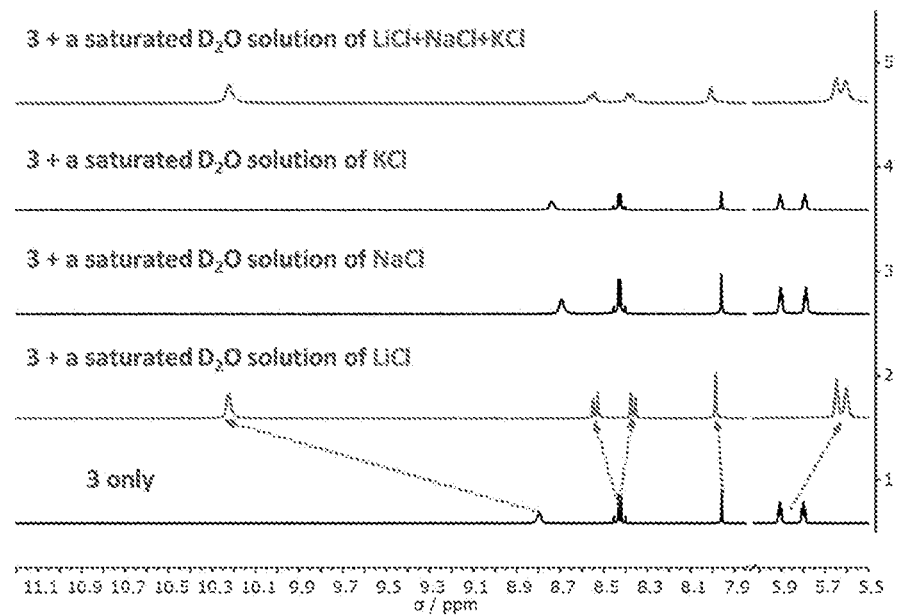
FIG. 44 shows partial $^1$H NMR spectra of a 3.0 mM solution of 3 in CDCl$_3$ recorded after exposure to D$_2$O, saturated LiCl in D$_2$O, saturated NaCl in D$_2$O, saturated KCl in D$_2$O, and saturated LiCl—NaCl—KCl in D$_2$O.
Figure 45:
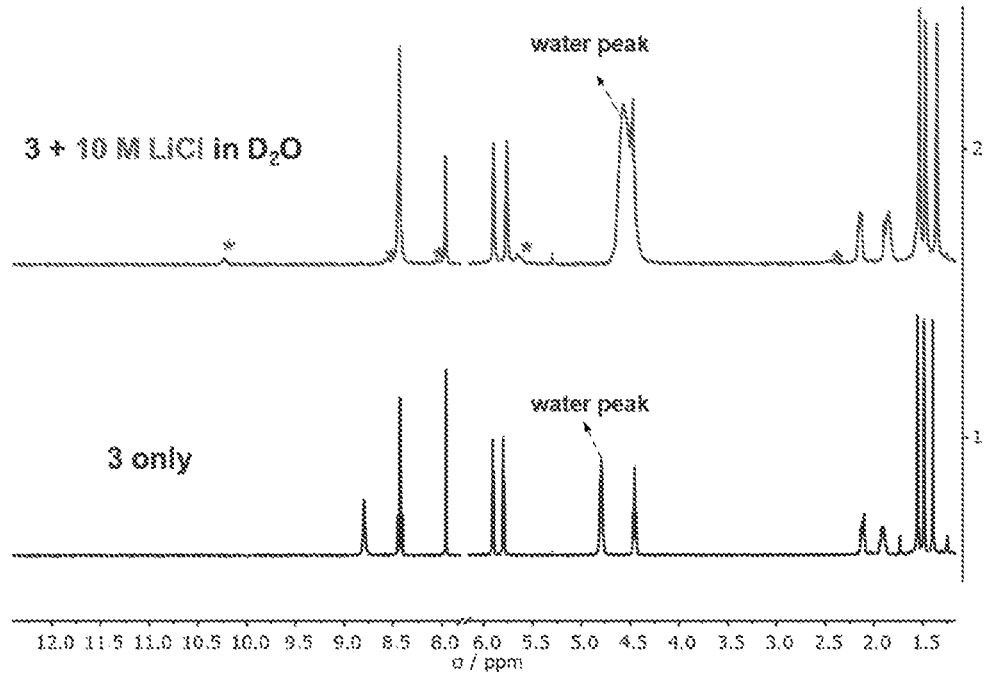
FIG. 45 shows partial $^1$H NMR spectra of a 3.0 mM solution of 3 in CDCl$_3$ recorded after exposure D$_2$O, and a 10 M solution of LiCl in D$_2$O.

Efforts were then made to assess whether 2 or 3 was capable of extracting LiCl under LLE conditions. When a solution of 2 in $C_6D_5NO_2$ (4.0 mM) is exposed to solutions of LiCl in $D_2O$ at concentrations varying from 1 M to 4 M, two sets of readily distinguishable proton signals, assigned to the free host 2 and the 2·LiCl complex, respectively, were observed. Slow exchange predominates, meaning the relative concentrations of the species in question could be measured via signal integration. Thus, the loading (of 2), which is defined as the molar percentage of extractant containing LiCl after exposure to the concentrated aqueous LiCl solution, was estimated to be ca. 12%, 20%, 27%, and 40% when solutions of 2 in $C_6D_5NO_2$ were exposed to 1 M, 2 M, 3 M, and 4 M LiCl solutions in $D_2O$, respectively (FIG. 40, square line markers). As expected, the loading increases as the source phase LiCl concentrations increase. For instance, nearly 100% loading was seen at a LiCl concentration of 10 M (FIG. 41. The analogous liquid-liquid extraction loading was also tested in the case of NaCl and KCl (FIGS. 40, 42 & 43). The selectivity proved inversely correlated with the cation hydration energies, i.e., KCl>NaCl>LiCl. However, in the case of 3, when a 3.0 mM solution of 3 in $CDCl_3$ was exposed to a saturated $D_2O$ solution of LiCl, all proton signals known to be diagnostic of $Cl^-$ binding and $Li^+$ complexation shifted downfield or upfield shifts in the expected manner relative to the $^1H$ NMR spectrum of free 3 in $D_2O$ saturated $CDCl_3$ (Table 6 and FIG. 44). These spectral changes were taken as evidence that LiCl was being extracted effectively (~100% receptor loading) from the $D_2O$ phase into chloroform. In contrast, exposure of 3 to saturated $D_2O$ solutions of NaCl or KCl under otherwise identical conditions produced no appreciable changes in the $^1H$ NMR spectrum. The extent of LiCl receptor loading dropped to ~15% when the concentration of LiCl in $D_2O$ was lowered to 10 M (FIG. 45). Thus, the overall efficacy is lower for 3 than for 2. However, selectivity of 3 is far greater than it is for 2.

TABLE 6

Change in the $^1H$ NMR Chemical Shifts for Receptor 3 (ppm) as Recorded upon Salt Extraction into $CDCl_3$ from an Aqueous Source Phase[a]

| proton | LiCl | NaCl | KCl | saturated LiCl + NaCl + KCl |
|---|---|---|---|---|
| NH | +1.43 | −0.10 | −0.05 | +1.43 |
| $H_a$ | +0.03 | 0.00 | 0.00 | +0.05 |
| $H_b$ | −0.05 | 0.00 | 0.00 | −0.03 |
| $H_c$ | +0.10 | 0.00 | 0.00 | +0.11 |
| $H_d$ | +0.19 | 0.00 | 0.00 | —[b] |
| $H_e$ | +0.33 | 0.00 | 0.33 | +0.33 |
| $H_f$ | −0.11 | −0.02 | −0.01 | −0.11 |
| $H_g$ | −0.20 | −0.01 | −0.01 | −0.19 |

[a]T = 295 K. See FIG. 33B for a hydrogen-labeling diagram. Negative values indicate upheld movement toward zero ppm. All spectra referenced to residue chloroform peak (7.26 ppm).
[b]Signal overlaps with the residual water peak.

In summary, the ion pair binding properties of a new hemispherand-strapped calix[4]pyrrole 2 and a phenanthroline-strapped calix[4]pyrrole 3 have been studied in detail. Receptor 2 proved capable of capturing LiCl, NaCl, KCl and CsC, while its congener 3 proved capable of complexing LiCl as confirmed by NMR spectroscopy, single-crystal structures, and DFT calculations. Further, 2 could be used to separate LiCl from a solid NaCl—KCl mixture containing only 1% of LiCl. Receptor 3 was able to strip LiCl from a solid NaCl—KCl mixture containing only 200 ppm of LiCl with 100% selectivity. When used as a extractant for LLE, 2 proved capable of extracting LiCl, NaCl and KCl into a bulk nitrobenzene phase at relatively low salt concentrations (<1 M), with the selectivity being KCl>NaCl>LiCl. Receptor 3 proved capable of extracting LiCl from an aqueous source phase into a chloroform receiving phase with 100% selectivity under conditions of near-saturation. Overall, these studies are expected to advance the understanding of design criteria needed to produce ion pair receptors targeted for the recognition and extraction of a given anion-cation salt combination.

Example 2: Synthesis, Characterization, and Methodology a. General Methods

All solvents and chemicals used were purchased from Sigma-Aldrich, TCI, or Acros and used without further purification. TLC analyses were carried out by using Sorbent Technologies silica gel (200 mesh) sheets. Column chromatography was performed on Sorbent silica gel 60 (40-63 µm). NMR spectra were recorded on a Varian Mercury 400 instrument. The NMR spectra were referenced to residual solvent peaks and the spectroscopic solvents were purchased from Cambridge Isotope Laboratories or Sigma-Aldrich. Electrospray ionization (ESI) mass spectra were recorded on a VG AutoSpec apparatus. X-ray crystallographic analyses were carried out on either a Rigaku AFC12 diffractometer equipped with a Saturn 724+ CCD with a graphite monochromator and a MoKα radiation source ($\lambda$=0.71075 Å) or an Agilent Technologies SuperNova Dual Source diffractometer using a µ-focused Cu Kα radiation source ($\lambda$=1.5418 Å) with collimating mirror monochromators. Further details of the structures and their refinement is given in a later section. Lithium concentrations were determined using an Agilent 7500ce quadrupole spectrometer using the following conditions: 1500 W forward RF power, 4 W reflected RF power, 15 L/min plasma gas flow, 0.9 L/min auxiliary gas flow, 0.90 L/min carrier nebulizer gas flow, 0.10 L/min make-up gas flow, spray chamber cooled to 2° C., and a peristaltic pump speed of 0.1 rpm. The $Na^+$ and $K^+$ cation concentrations were analyzed using an octopole collision-reaction system, with He being employed as a collision gas to remove matrix and plasma-related interferences, and to limit detected intensities. Key results are given in Tables 1 & 4 and are described herein.

b. Synthesis

Figures 2A, 2B:
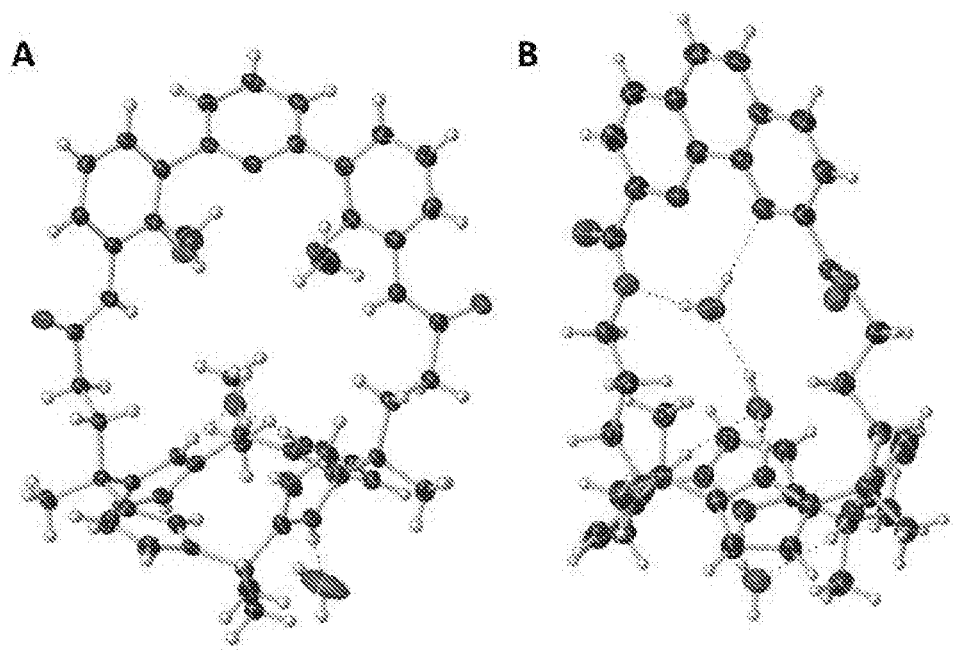
FIGS. 2A & 2B show a single-crystal structures of (FIG. 2A) 2·(H₂O)₂ and (FIG. 2B) 3·(H₂O)₃. Displacement ellipsoids are scaled to the 50% probability level. Most solvent molecules have been removed for clarity. Dashed lines are indicative of presumed H-bonding interactions.

Receptors 2 and 3 were synthesized using a procedure similar to that used to prepare compound 1 (He et al., 2016). As shown in Scheme 2, precursor S5 was prepared in 89% yield via a tetrakis(triphenylphosphine)palladium(0)-catalyzed Suzuki-Miyaura cross-coupling reaction using 6-amino-2-(4,4,5,5-tetramethyl-1,3,2-dioxaborolan-2-yl) anisole (S3) and 2,6-dibromopyridine (S4) as the starting materials. Condensation of S5 and S6 in the presence of N-ethyl-N'-(3-dimethylaminopropyl)carbodiimide hydrochloride (EDCI·HCl) and pyridine in CH$_2$Cl$_2$ then gave compound S7 in 49% yield. Subsequent cyclization of the precursor of 2 in acetone in the presence of excess BF$_3$·Et$_2$O yielded a precipitate that proved to be 2·Et$_3$N·HF (FIGS. 1A & 1B). Additional quantities could be recovered from the mother liquor via flash column chromatography over silica gel. After the Et$_3$N·HF was removed by washing with water, compound 2 was obtained directly in 32% yield without a need for further purification. In a similar way, EDCI coupling reaction of S8 with S9 in the presence of N,N-diisopropylethylamine (DIPEA) and hydroxybenzotriazole (HBOt) in DMF at room temperature gave precursor S10 in 42% yield, which was then subjected to cyclization with acetone in the presence of BF$_3$·OEt$_2$ to give the target compound 3 in 17% yield. Compounds 2 and 3 were fully characterized by standard spectroscopic means, as well as by single crystal X-ray diffraction analysis (FIGS. 2A & 2B).

Scheme 2. Synthesis of 2.

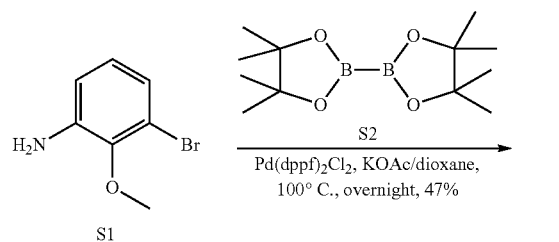

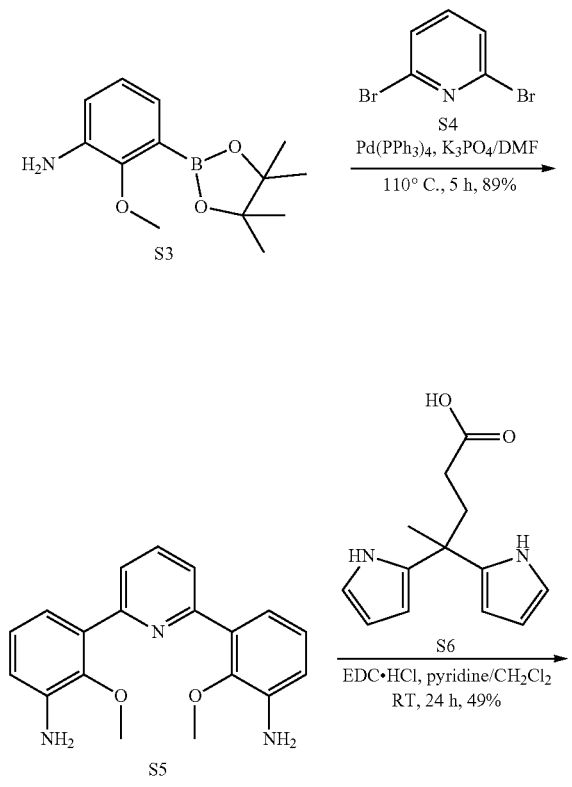

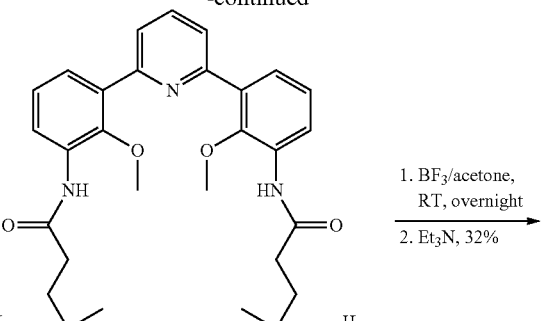

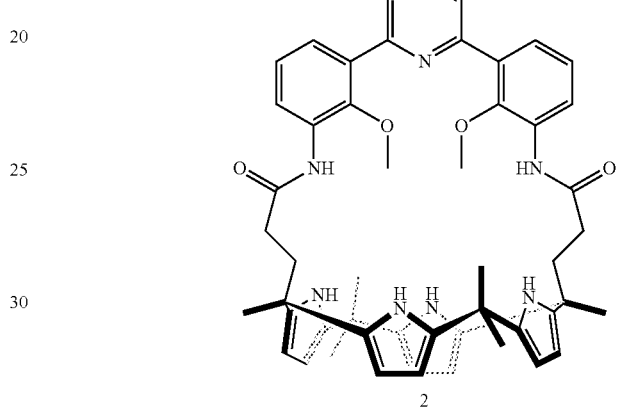

Compounds S2 and S4 are commercially available and compounds S1 and S6 were prepared according to literature procedures (He et al., 2016, and Chien et al., 1934).

Synthesis of S3

A 500 ml round-bottomed flask was charged with S1 (6.61 g, 32.7 mmol), S2 (12.46 g, 49.1 mmol), Pd(dppf)$_2$Cl$_2$ (1.05 g, 1.1 mmol), KOAc (9.62 g, 98.2 mmol) and 1,4-dioxane (200 ml), degassed and refilled with N$_2$. The resulting solution was heated to 100° C. under an N$_2$ atmosphere and then stirred overnight. After cooled to room temperature, the solution was quenched with water (10 ml) and diluted with ethyl acetate (150 ml). The resulting mixture was washed with brine (3×100 ml), dried with Na$_2$SO$_4$. After the solvent was removed in vacuo, the residue was subjected to flash column over silica gel eluting with ethyl acetate/hexane (1:3, v/v) to obtain compound S3 (3.83 g, 47%) as off-white solid. $^1$H NMR (400 MHz, CDCl$_3$, ppm): δ 7.11 (d, J=7.1 Hz, 1H, ArH), 6.93 (t, J=6.9 Hz, 1H, ArH), 6.86 (d, J=6.9 Hz, 1H, ArH), 3.82 (br., 2H, NH$_2$), 3.81 (s, 3H, OMe), 1.36 (s, 12H, Me); $^{13}$C NMR (100 MHz, CDCl$_3$, ppm): δ 152.7, 139.6, 126.1, 124.3, 119.1, 83.6, 24.9. The carbon directly attached to the boron atom was not detected, likely due to quadrapolar relaxation; HRMS (ESI) m/z 250.1614 [M+H]$^+$ calcd for C$_{13}$H$_{22}$BNO$_3$, found 250.1609.

Synthesis of 3,3'-(pyridine-2,6-diyl)bis(2-methoxyaniline) (S5)

Compounds S3 (3.67 g, 14.7 mmol), S2 (1.75 g, 7.3 mmol), Pd(PPh$_3$)$_4$ (509 mg, 0.4 mmol), and K$_3$PO$_4$ (10.23 g, 44.1 mmol) were dissolved in dry DMF (150 ml), heated to 110° C. under an N$_2$ atmosphere, and then stirred for 5 h. After allowing the reaction mixture to cool to room temperature, the mixture was diluted with ethyl acetate (150 ml). The resulting solution was washed with water (3×200 ml). The combined organic phase was dried over anhydrous Na$_2$SO$_4$ for 2 h. After evaporation off the volatiles under reduced pressure, the residue was subjected to flash column over silica gel eluting with ethyl acetate (EA)/hexanes (1:2, v/v) to obtain compound S5 (0.92 g, 63%) as an off-white solid. $^1$H NMR (400 MHz, CDCl$_3$, ppm): δ 7.73-7.80 (m, 3H, ArH), 7.24 (dd, J=7.8, 1.6 Hz, 2H, ArH), 7.03 (t, J=7.8 Hz, 2H, ArH), 6.79 (dd, J=7.8, 1.6 Hz, 2H, ArH), 3.94 (br, J=4H, NH$_2$), 3.54 (s, 6H, OMe); $^{13}$C NMR (100 MHz, CDCl$_3$, ppm): δ 156.0, 145.3, 140.2, 136.3, 133.8, 124.8, 122.5, 120.8, 116.3, 60.18; HRMS (ESI) m/z 322.1556 [M+H]$^+$ calcd for C$_{19}$H$_{20}$N$_3$O$_2$, found 322.1551.

Synthesis of Compound S7

To a mixture of compound S5 (6.02 g, 18.8 mmol), S6 (9.57 g, 41.3 mmol), and EDCI·HCl (10.80 g, 56.3 mmol) in CH$_2$Cl$_2$ (DCM; 400 ml) 15 ml of pyridine was added. The resulting solution was stirred at room temperature under an N$_2$ atmosphere for 24 h. After the volatiles were removed under reduced pressure, the residue was subjected to column chromatography over silica gel eluting with ethyl acetate/hexanes (1/4, v/v) to give 7.77 g (55% yield) of S7 as an off-white solid. $^1$H NMR (400 MHz, CD$_2$Cl$_2$, ppm): δ 8.37 (d, J=8.4 Hz, 2H, ArH), 8.11 (br., 4H, pyrrole-NH), 7.86 (br., 2H, CONH), 7.84-7.72 (m, 3H, ArH), 7.49 (d, J=7.5 Hz, 2H, ArH), 7.19 (t, J=7.2 Hz, 2H, ArH), 6.70-6.58 (m, 4H, ArH), 6.20-6.02 (m, 8H, pyrrole-H), 3.50 (s, 6H, OMe), 2.50-2.39 (m, 4H, CH$_2$), 2.38-2.61 (m, 4H, CH$_2$), 1.62 (s, 6H, CH$_3$); $^{13}$C NMR (100 MHz, CD$_2$Cl$_2$, ppm): δ 171.7, 155.9, 147.2, 137.5, 137.2, 133.1, 132.4, 126.0, 124.7, 123.0, 120.9, 117.6, 108.1, 105.1, 61.7, 39.1, 36.3, 33.6, 26.5; HRMS (ESI) m/z 750.3762 [M+H]$^+$ calcd for C$_{45}$H$_{48}$N$_7$O$_4$, found 750.3767.

Synthesis of Compound 2

BF$_3$·Et$_2$O (1.0 ml) was added dropwise to a solution of precursor S7 (2.54 g, 3.4 mmol) in acetone (900 ml) at room temperature (RT). The reaction solution was stirred at RT overnight. Then triethylamine (30 ml) was added to quench the reaction. Most solvent was removed to afford some white solid, which was filtered off. The filter cakes were washed with excess acetone (the solid was found to be 2·TEA·HF as evidenced by a subsequent crystal structure), water, and acetone to give 0.51 g of pure 2. The filtrate residue was further purified by column chromatography over silica gel (eluent: ethyl acetate/hexanes (1/3, v/v)) to give another 0.39 g of 2. A total of 0.90 g (32% yield) of 2 as an off-white solid was obtained in this way. $^1$H NMR (400 MHz, CD$_2$Cl$_2$/CD$_3$OD (9:1, v/v), ppm): δ 9.25 (br., 4H, pyrrole-NH), 8.40 (d, J=8.4 Hz, 2H, ArH), 7.99 (t, J=8.0 Hz, 1H, ArH), 7.89 (s, 2H, CONH), 7.52 (d, J=7.5 Hz, 2H, ArH), 7.11 (t, J=7.1 Hz, 2H, ArH), 7.00 (d, J=7.1 Hz, 2H, ArH), 5.88 (s, 8H, pyrrole-CH), 3.36 (s, 6H, OMe), 2.39-2.19 (m, 4H, CH$_2$), 2.01-1.82 (m, 4H, CH$_2$), 1.79-1.35 (m, 18H, CH$_3$); $^{13}$C NMR (100 MHz, CD$_2$Cl$_2$/CD$_3$OD (9:1, v/v), ppm): δ 173.0, 157.0, 146.5, 139.5, 138.7, 136.8, 132.7, 131.8, 125.6, 123.9, 122.2, 119.6, 105.1, 102.1, 61.3, 40.8, 39.0, 35.2, 34.3, 27.7, 27.1, 26.2; HRMS (ESI) m/z 830.4388 [M+H]$^+$ calcd for C$_{51}$H$_{56}$N$_7$O$_4$, found 830.4402.

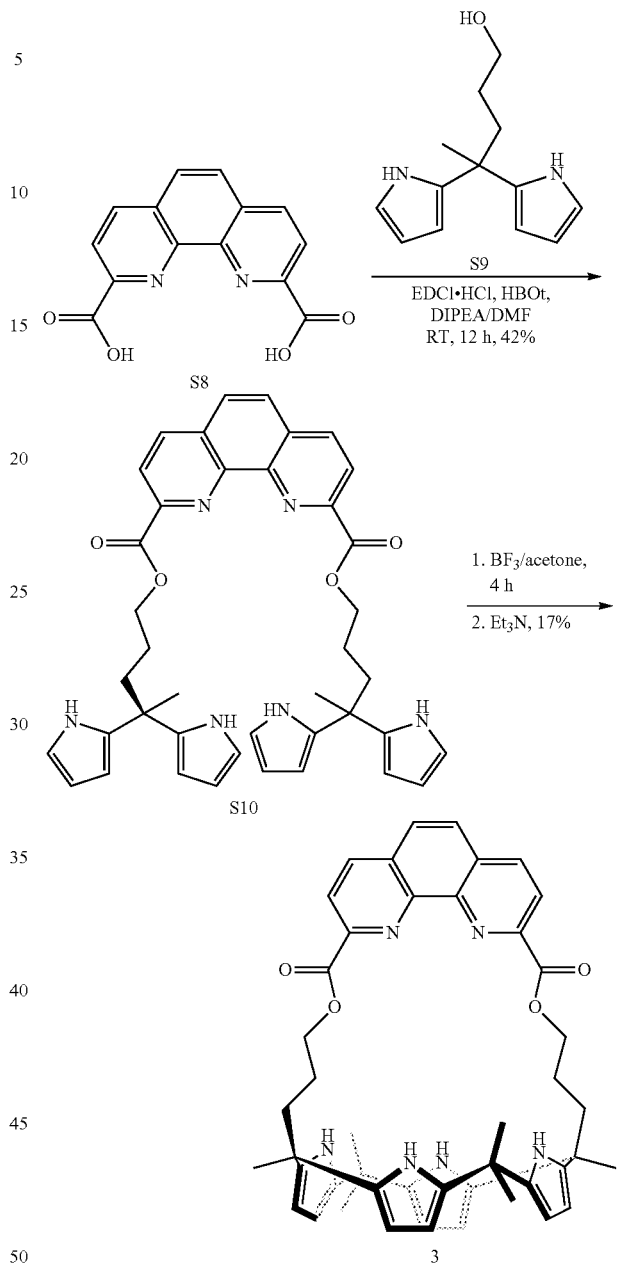

Scheme 3. Synthesis of 3.

A general synthetic route to compound 3 is shown above. Compounds S8 and S9 were prepared according to literature procedures (Chandler et al., 1981, and Yoon et al., 2008)

Synthesis of Compound S10

To a solution of 2,9-phenantholinedicarboxylic acid (2.00 g, 7.5 mmol), 5-(3-hydroxypropyl)-5-methyl dipyrromethane (S9) (3.25 g, 14.9 mmol), EDCI (1-ethyl-3-(3-dimethylaminopropyl)-carbodiimide, 3.00 g, 15.7 mmol) and HBOt (hydroxybenzotriazole, 2.12 g, 14.3 mmol) in dry DMF (50 ml) was added DIPEA (N,N-diisopropylethylamine, 0.20 ml, 1.2 mmol) via syringe. The resulting solution was stirred overnight at room temperature and concentrated under reduced pressure to give a brownish oil. Column chromatography over silica gel (eluent: ethyl acetate/ hexanes (2/1, v/v)) gave 2.10 g (42% yield) of S10 as a white solid. $^1$H NMR (300 MHz, DMSO-$d_6$, ppm): δ 10.35 (br s, 4H, pyrrole-NH), 8.71 (d, J=9.0 Hz, 2H, ArH (phenanthroline)), 8.39 (d, J=9.0 Hz, 2H, ArH (phenanthroline)), 8.19 (s, 2H, ArH (phenanthroline), 6.60 (m, 4H, ArH (pyrrole)), 5.88 (m, 4H, ArH (pyrrole)), 5.78 (m, 4H, ArH (pyrrole)), 4.36 (t, J=6.0 Hz, 4H, COOCH2), 2.14 (m, 4H, CH$_2$CH$_2$CH$_2$), 1.69-1.63 (m, 4H, CH$_2$CH$_2$CH$_2$), 1.60 (s, 6H, CH$_3$); $^{13}$C NMR (75 MHz, DMSO-$d_6$, ppm): δ 165.2, 148.3, 145.6, 138.5, 131.0, 128.9, 124.2, 117.0, 106.8, 104.4, 66.4, 55.4, 37.3, 25.6, 24.6; HRMS (ESI) m/z 669.3189 [M+H]$^+$ calcd for C$_{40}$H$_{41}$N$_6$O$_4$, found 669.3185.

Synthesis of Compound 3

To compound S10 (2.00 g, 3.0 mmol) in acetone (700 ml) was added BF$_3$·OEt$_2$ (1.0 ml, 8.1 mmol) in one portion. The resulting solution was stirred for 4 h at room temperature and then quenched with triethylamine (5 ml). Evaporation of the volatile components in vacuo afforded a brownish solid. To this crude product, dichloromethane (100 ml), water (100 ml) and triethylamine (5 ml) were added and the organic phase was separated off and washed twice with water (100 ml). The organic layer was dried over anhydrous MgSO$_4$ and evaporated in vacuo to give a brownish solid. Recrystallization from a mixture of dichloromethane and methanol (9/1), following column chromatography over silica gel (acetone:dichloromethane=1:4 (v/v)), gave 0.39 g (17% yield) of 1 as a yellowish solid: $^1$H NMR (300 MHz, CDCl$_3$, ppm): δ 8.70 (br s, 4H, pyrrole-NH), 8.42 (dd, J=9.0 Hz, 4H, ArH (phenanthroline)), 7.96 (s, 2H, ArH (phenanthroline), 5.91 (m, 4H, ArH (pyrrole)), 5.79 (m, 4H, ArH (pyrrole)), 4.46 (t, J=6.0 Hz, 4H, COOCH$_2$), 2.14 (m, 4H, CH$_2$CH$_2$CH$_2$), 1.88 (m, 4H, CH$_2$CH$_2$CH$_2$), 1.55 (s, 6H, CH$_3$), 1.48 (s, 6H, CH$_3$), 1.39 (s, 6H, CH$_3$); $^{13}$C NMR (75 MHz, DMSO-$d_6$, ppm): δ 165.2, 148.4, 145.6, 138.5, 131.0, 128.9, 124.2, 117.0, 106.8, 104.4, 66.4, 55.4, 38.8, 37.2, 25.6, 24.6; HRMS (ESI) m/z 749.3815 [M+H]$^+$ calcd for C$_{46}$H$_{49}$N$_6$O$_4$, found 749.3810. This compound was further characterized via a single crystal X-ray diffraction analysis.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

Anderson, *Practical Process Research & Development—A Guide for Organic Chemists*, 2$^{nd}$ ed., Academic Press, New York, 2012.
Chandler et al. *J. Heterocyclic. Chem.*, 18:599, 1981.
Chen et al., *Tetrahedron Lett*, 41:4815-4818, 2000.
Chien et al., *J. Am. Chem. Soc.*, 56:1787-1792, 1934.
Cram et al., *Angew. Chem. Int. Ed.*, 25:1039-1057, 1986.
Cram et al., *J. Am. Chem. Soc.*, 107:3645-3657, 1985.
Cram, *Angew. Chem. Int. Ed.*, 25:1039-1057, 1986.
Ericksen et al., in *Lithium Needs and Resources*, Pergamon, pp. 355-363, 1978.
Gale, *Coord. Chem. Rev.*, 240:191-221, 2003.
Grote et al., *J. Am. Chem. Soc.*, 125:13638-13639, 2003.
*Handbook of Pharmaceutical Salts: Properties, and Use*, Stahl and Wermuth Eds., Verlag Helvetica Chimica Acta, 2002.
Hano et al., *Solvent Extr. Ion Exc.*, 10:195-206, 1992.
He et al., *J. Am. Chem. Soc.*, 138:9779-9782, 2016.
Kara et al., *Procedia CIRP*, 29:752-757, 2015.
Kim and Sessler, *Acc. Chem. Res.*, 47:2525-2536, 2014.
Kim and Sessler, *Chem. Soc. Rev.*, 39:3784-3809, 2010.
Kirkovits et al., *J. Incl. Phenom. Macro.*, 41:69-75, 2001.
Kobiro, *Coord. Chem. Rev.*, 148:135-149, 1996.
Kollman et al., *J. Am. Chem. Soc.*, 107:2212-2219, 1985.
Lide, *CRC Handbook*, 75$^{th}$ Ed., pp. 12-13.
Mahoney et al., *Inorg. Chem.*, 43:7617-7621, 2004.
Marcus, *J. Chem. Soc. Faraday Trans.*, 87:2995-2999, 1991.
McConnell and Beer, *Angew. Chem. Int. Ed.*, 51:5052-5061, 2012.
Morita et al., *Heterocycles*, 70:389-421, 2006.
Paquette and Tae, *J. Am. Chem. Soc.*, 123:4974-4984, 2001.
Paquette et al., *Angew. Chem. Int. Ed.*, 38:1409-1411, 1999.
Piotrowski and Severin, *Proc. Natl. Acad. Sci. USA*, 99:4997-5000, 2002.
Pranolo et al., *Hydrometallurgy*, 154:33-39, 2015.
Reagan-Shaw et al., *FASEB J.*, 22(3):659-661, 2008.
Sharma et al., *Sep. Sci. Technol.*, 51:2242-2254, 2016.
Smith (Ed.: K. Gloe, Antonioli, B., Eds.; Kluwer:), Springer Netherlands, London, U.K., pp. 137-152, 2005.
Smith, *March's Advanced Organic Chemistry: Reactions, Mechanisms, and Structure*, 7$^{th}$ Ed., Wiley, 2013.
Swain, *Purif. Technol.*, 172:388-403, 2017.
Torrejos et al., *Hydrometallurgy*, 164:362-371, 2016.
Tsuchiya et al., *J. Am. Chem. Soc.*, 124:4936-4937, 2002
Yoon et al., *Angew. Chem., Int. Ed.*, 47:5038, 2008.
Zhang et al., *Hydrometallurgy*, 175:35-42, 2018.

What is claimed is:

1. A compound of the formula:

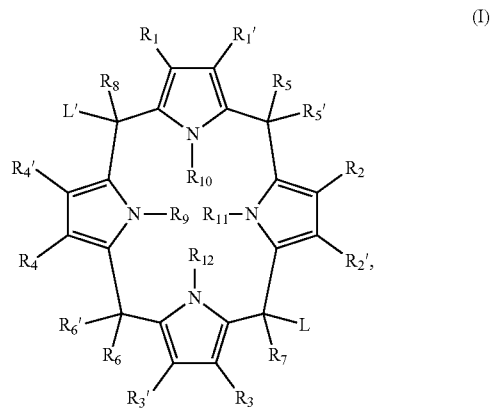

wherein:
R$_1$, R$_1$', R$_2$, R$_2$', R$_3$, R$_3$', R$_4$, and R$_4$' are each independently hydrogen, hydroxy, amino, cyano, or halo; or alkyl$_{(C≤6)}$, alkenyl$_{(C≤6)}$, alkynyl$_{(C≤6)}$, acyloxy$_{(C≤6)}$, alkoxy$_{(C≤6)}$, alkylamino$_{(C≤6)}$, dialkylamino$_{(C≤12)}$, amido$_{(C≤6)}$, or a substituted version of any of these groups; or one of these groups is attached to a solid support or a fluorophore;

$R_5$, $R_5'$, $R_6$, $R_6'$, $R_7$, and $R_8$ are each independently hydrogen or alkyl$_{(C≤12)}$, cycloalkyl$_{(C≤12)}$, cycloalkenyl(C=12), alkenyl$_{(C≤12)}$, alkynyl$_{(C≤12)}$, aryl$_{(C≤12)}$, heteroalkyl$_{(C≤12)}$, heterocycloalkyl$_{(C≤12)}$, alkoxy$_{(C≤12)}$, alkylamino$_{(C≤12)}$, dialkylamino$_{(C≤18)}$, amido$_{(C≤12)}$, or a substituted version of any of these groups; or one of these groups is attached to a solid support or a fluorophore;

$R_9$, $R_{10}$, $R_{11}$, and $R_{12}$ are hydrogen, alkyl$_{(C≤6)}$, or substituted alkyl$_{(C≤6)}$;

L and L' are taken together and form a group of the formula:

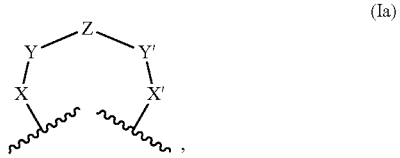

(Ia)

wherein:

X and X' are each independently alkanediyl$_{(C≤8)}$, cycloalkanediyl$_{(C≤8)}$, alkenediyl$_{(C≤8)}$, alkynediyl$_{(C≤8)}$, arenediyl$_{(C≤8)}$, or a substituted version of any of these groups;

Y and Y' are each independently —O—, —C(O)—, —C(O)O—, —S(O)—, —S(O)$_2$O—, —C(O)NR$_a$—, or —S(O)$_2$NR$_b$—, wherein:

R$_a$ and R$_b$ are each independently hydrogen, alkyl$_{(C≤6)}$, or substituted alkyl$_{(C≤6)}$; or one or more of these groups is attached to a solid support or a fluorophore;

Z is a group of the formula:

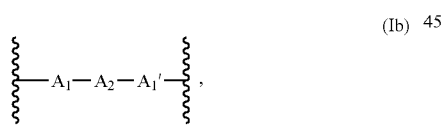

(Ib)

wherein:

A$_1$ and A$_1'$ are each independently arenediyl$_{(C≤8)}$, substituted arenediyl$_{(C≤8)}$, heteroarenediyl$_{(C≤8)}$ or substituted heteroarenediyl$_{(C≤8)}$; and A$_2$ is heteroarenediyl$_{(C≤8)}$ or substituted heteroarenediyl$_{(C≤8)}$; or Z is arenediyl$_{(C≤24)}$, substituted arenediyl$_{(C≤24)}$, heteroarenediyl$_{(C≤24)}$, or substituted heteroarenediyl$_{(C≤24)}$, wherein the group comprises at least 3 fused rings;

wherein when a chemical group is used with the "substituted" modifier, one or more hydrogen atom has been replaced, independently at each instance, by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$;

or a salt thereof.

2. The compound of claim 1, wherein the compound is further defined as:

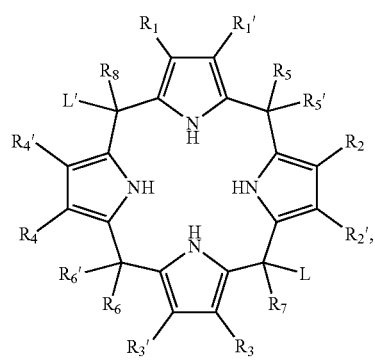

(II)

wherein:

$R_1$, $R_1'$, $R_2$, $R_2'$, $R_3$, $R_3'$, $R_4$, and $R_4'$ are each independently hydrogen, hydroxy, amino, cyano, or halo; or alkyl$_{(C≤6)}$, alkenyl$_{(C≤6)}$, alkynyl$_{(C≤6)}$, acyloxy$_{(C≤6)}$, alkoxy$_{(C≤6)}$, alkylamino$_{(C≤6)}$, dialkylamino$_{(C≤12)}$, amido$_{(C≤6)}$, or a substituted version of any of these groups;

$R_5$, $R_5'$, $R_6$, $R_6'$, $R_7$, and $R_8$ are each independently hydrogen or alkyl$_{(C≤6)}$, alkenyl$_{(C≤6)}$, alkynyl$_{(C≤6)}$, or a substituted version of any of these groups;

L and L' are taken together and form a group of the formula:

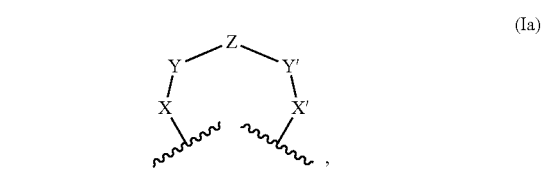

(Ia)

wherein:

X and X' are each independently alkanediyl$_{(C≤8)}$, alkenediyl$_{(C≤8)}$, alkynediyl$_{(C≤8)}$, or a substituted version of any of these groups;

Y and Y' are each independently —C(O)—, —C(O)O—, —S(O)—, —S(O)$_2$O—, —C(O)NR$_a$—, or —S(O)$_2$NR$_b$—, wherein:

R$_a$ and R$_b$ are each independently hydrogen, alkyl$_{(C≤6)}$, or substituted alkyl$_{(C≤6)}$;

Z is a group of the formula:

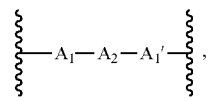

(Ib)

wherein:

A$_1$ and A$_1'$ are each independently arenediyl$_{(C≤8)}$, substituted arenediyl$_{(C≤8)}$, heteroarenediyl$_{(C≤8)}$ or substituted heteroarenediyl$_{(C≤8)}$; and A₂ is heteroarenediyl$_{(C≤8)}$ or substituted heteroarenediyl$_{(C≤8)}$; or Z is arenediyl$_{(C≤24)}$, substituted arenediyl$_{(C≤24)}$, heteroarenediyl$_{(C≤24)}$, or substituted heteroarenediyl$_{(C≤24)}$, wherein the group comprises at least 3 fused rings;

or a salt thereof.

3. The compound of claim 1, wherein the compound is further defined:

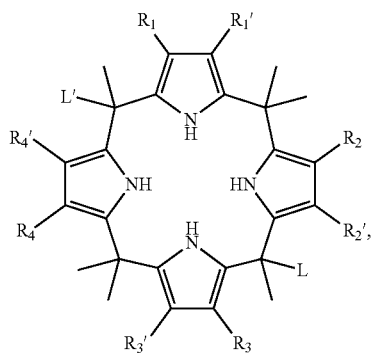

(III)

wherein:
R₁, R₁', R₂, R₂', R₃, R₃', R₄, and R₄' are each independently hydrogen, hydroxy, amino, cyano, or halo; or alkyl$_{(C≤6)}$, alkenyl$_{(C≤6)}$, alkynyl$_{(C≤6)}$, acyloxy$_{(C≤6)}$, alkoxy$_{(C≤6)}$, alkylamino$_{(C≤6)}$, dialkylamino$_{(C≤12)}$, amido$_{(C≤6)}$, or a substituted version of any of these groups;

L and L' are taken together and form a group of the formula:

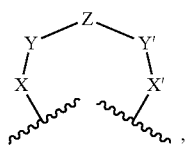

(Ia)

wherein:
X and X' are each independently alkanediyl$_{(C≤8)}$, alkenediyl$_{(C≤8)}$, alkynediyl$_{(C≤8)}$, or a substituted version of any of these groups;

Y and Y' are each independently —C(O)—, —C(O)O—, —S(O)—, —S(O)₂O—, —C(O)NR$_a$—, or —S(O)₂NR$_b$—, wherein:
R$_a$ and R$_b$ are each independently hydrogen, alkyl$_{(C≤6)}$, or substituted alkyl$_{(C≤6)}$;

Z is a group of the formula:

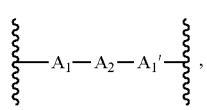

(Ib)

wherein:
A₁ and A₁' are each independently arenediyl$_{(C≤8)}$, substituted arenediyl$_{(C≤8)}$, heteroarenediyl$_{(C≤8)}$ or substituted heteroarenediyl$_{(C≤8)}$; and A₂ is heteroarenediyl$_{(C≤8)}$ or substituted heteroarenediyl$_{(C≤8)}$; or Z is arenediyl$_{(C≤24)}$, substituted arenediyl$_{(C≤24)}$, heteroarenediyl$_{(C≤24)}$, or substituted heteroarenediyl$_{(C≤24)}$, wherein the group comprises at least 3 fused rings;

or a salt thereof.

4. The compound of claim 1, wherein the compound is further defined:

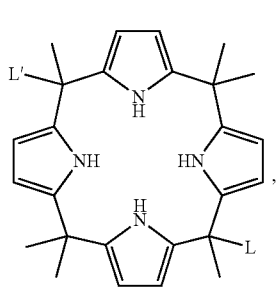

(IV)

wherein:
L and L' are taken together and form a group of the formula:

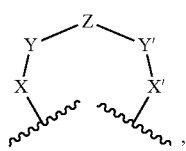

(Ia)

wherein:
X and X' are each independently alkanediyl$_{(C≤8)}$, alkenediyl$_{(C≤8)}$, alkynediyl$_{(C≤8)}$, or a substituted version of any of these groups;

Y and Y' are each independently —C(O)—, —C(O)O—, —S(O)—, —S(O)₂O—, —C(O)NR$_a$—, or —S(O)₂NR$_b$—, wherein:
R$_a$ and R$_b$ are each independently hydrogen, alkyl$_{(C≤6)}$, or substituted alkyl$_{(C≤6)}$;

Z is a group of the formula:

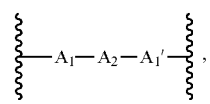

(Ib)

wherein:
A₁ and A₁' are each independently arenediyl$_{(C≤8)}$, substituted arenediyl$_{(C≤8)}$, heteroarenediyl$_{(C≤8)}$ or substituted heteroarenediyl$_{(C≤8)}$; and A₂ is heteroarenediyl(c) or substituted heteroarenediyl$_{(C≤8)}$; or Z is arenediyl$_{(C≤24)}$, substituted arenediyl$_{(C≤24)}$, heteroarenediyl$_{(C≤24)}$, or substituted heteroarenediyl$_{(C≤24)}$, wherein the group comprises at least 3 fused rings;

or a salt thereof.

5. The compound of claim 1, wherein the compound is further defined:

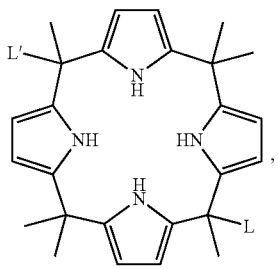
(IV)

wherein:
L and L' are taken together and form a group of the formula:

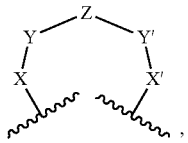
(Ia)

wherein:
X and X' are each independently alkanediyl$_{(C≤8)}$, alkenediyl$_{(C≤8)}$, alkynediyl$_{(C≤8)}$, or a substituted version of any of these groups;
Y and Y' are each independently —C(O)—, —C(O)O—, —S(O)—, —S(O)$_2$O—, —C(O)NR$_a$—, or —S(O)$_2$NR$_b$—, wherein:
R$_a$ and R$_b$ are each independently hydrogen, alkyl$_{(C≤6)}$, or substituted alkyl$_{(C≤6)}$;
Z is a group of the formula:

$$\text{\textbraceleft}\!—A_1—A_2—A_1'—\text{\textbraceright}$$ (Ib)

wherein:
A$_1$ and A$_1$' are each independently arenediyl$_{(C≤8)}$, substituted arenediyl$_{(C≤8)}$, heteroarenediyl$_{(C≤8)}$ or substituted heteroarenediyl$_{(C≤8)}$; and
A$_2$ is heteroarenediyl$_{(C≤8)}$ or substituted heteroarenediyl$_{(C≤8)}$;
or a salt thereof.

6. The compound of claim 1, wherein the compound is further defined:

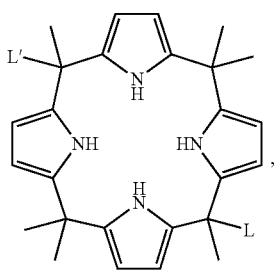
(IV)

wherein:
L and L' are taken together and form a group of the formula:

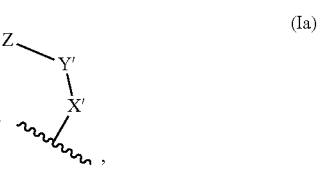
(Ia)

wherein:
X and X' are each independently alkanediyl$_{(C≤8)}$, alkenediyl$_{(C≤8)}$, alkynediyl$_{(C≤8)}$, or a substituted version of any of these groups;
Y and Y' are each independently —C(O)—, —C(O)O—, —S(O)—, —S(O)$_2$O—, —C(O)NR$_a$—, or —S(O)$_2$NR$_b$—, wherein:
R$_a$ and R$_b$ are each independently hydrogen, alkyl$_{(C≤6)}$, or substituted alkyl$_{(C≤6)}$; and
Z is arenediyl$_{(C≤24)}$, substituted arenediyl$_{(C≤24)}$, heteroarenediyl$_{(C≤24)}$, or substituted heteroarenediyl$_{(C≤24)}$, wherein the group comprises at least 3 fused rings;
or a salt thereof.

7. The compound of claim 1, wherein X and X' are both alkanediyl$_{(C≤8)}$ or substituted alkanediyl$_{(C≤8)}$.

8. The compound of claim 7, wherein X and X' are both ethanediyl or propanediyl.

9. The compound of claim 1, wherein Y and Y' are both —C(O)O— or —C(O)NR$_a$—.

10. The compound of claim 1, wherein A$_1$ and A$_1$' are both the same.

11. The compound of claim 10, wherein A$_1$ and A$_1$' are both arenediyl$_{(C≤8)}$ or substituted arenediyl$_{(C≤8)}$.

12. The compound of claim 1, wherein A$_2$ is heteroarenediyl$_{(C≤8)}$.

13. The compound of claim 1, wherein Z is substituted arenediyl$_{(C≤24)}$, heteroarenediyl$_{(C≤24)}$, or substituted heteroarenediyl$_{(C≤24)}$, wherein the group comprises at least 3 fused rings.

14. The compound of claim 13, wherein Z is heteroarenediyl$_{(C≤24)}$, wherein the group comprises at least 3 fused rings.

15. The compound of claim 14, wherein Z is heteroarenediyl$_{(C≤18)}$, wherein the group comprises 3 fused rings and contains at least two nitrogen atoms.

16. The compound of claim 1, wherein the compound is further defined:

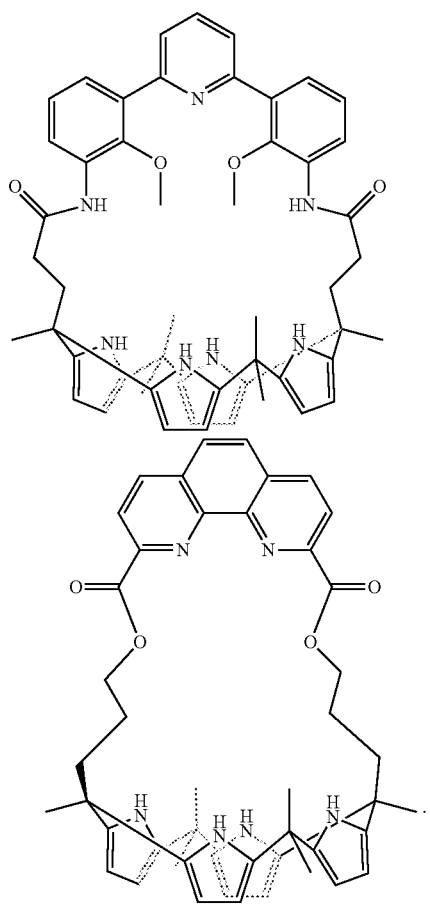
17. A composition comprising (A) a compound of claim 1; and (B) a salt.
18. The composition of claim 17, wherein the salt comprises an alkali metal cation.
19. The composition of claim 17, wherein the compound is defined as:
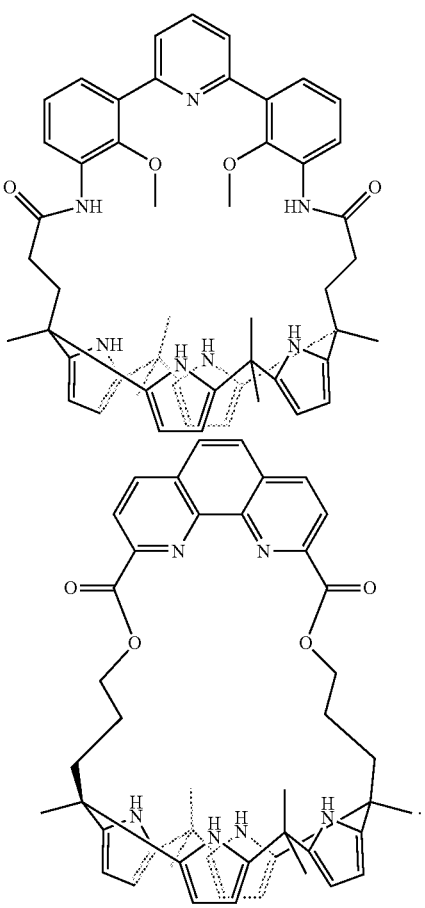
or
or